United States Patent
Gueziec et al.

[11] Patent Number: 5,951,475
[45] Date of Patent: Sep. 14, 1999

[54] METHODS AND APPARATUS FOR REGISTERING CT-SCAN DATA TO MULTIPLE FLUOROSCOPIC IMAGES

[75] Inventors: Andre Pierre Gueziec, Mamaroneck, N.Y.; Peter Kazanzides, Sacramento, Calif.; Russell H. Taylor, Severna Park, Md.

[73] Assignee: International Business Machines Corporation, Armonk, N.Y.

[21] Appl. No.: 08/936,935

[22] Filed: Sep. 25, 1997

[51] Int. Cl.[6] ......................................................... A61B 6/00
[52] U.S. Cl. ............................ 600/425; 378/42; 378/207; 382/285; 382/294; 128/922
[58] Field of Search ....................................... 600/425, 407, 600/473, 414, 417; 378/205, 206, 207, 42, 190; 606/130; 382/128, 132, 285, 294; 901/14; 356/395–397, 375

[56] References Cited

U.S. PATENT DOCUMENTS

| | | |
|---|---|---|
| 4,005,527 | 2/1977 | Wilson et al. . |
| 4,127,109 | 11/1978 | Fourney et al. . |
| 4,638,799 | 1/1987 | Moore . |
| 4,791,934 | 12/1988 | Brunnett . |
| 4,841,967 | 6/1989 | Chang et al. . |
| 4,855,928 | 8/1989 | Yamanaka . |
| 4,860,331 | 8/1989 | Williams et al. . |
| 5,050,608 | 9/1991 | Watanabe et al. . |
| 5,154,179 | 10/1992 | Ratner . |
| 5,216,700 | 6/1993 | Cherian . |

(List continued on next page.)

OTHER PUBLICATIONS

"Surgical Instrument Guidance Using Synthesized Anatomical Structures", Alan Liu et al., MRCAS'97 Grenoble, France, Mar. 1997, pp. 99–108.

"Intra–Operative Registration For Percutaneous Surgery", P. Potamianos, et al., pp. 156–164, Oct. 1995.

"Principle Warps: Thin–Plate Splines and the Decomposition of Deformations", Fred L. Bookstein, IEEE, Translations on Pattern Analysis and Machine Intelligence, vol. II, No. 6, Jun. 1989, pp. 567–585.

"Stereo Matching Of Skull Landmarks", Byung–Uk Lee, Jun. 1991, 71 pages.

(List continued on next page.)

*Primary Examiner*—William E. Kamm
*Assistant Examiner*—Shawna J Shaw
*Attorney, Agent, or Firm*—Jay P. Sbrollini, Esq.; Perman & Green, LLP

[57] ABSTRACT

A method and system is disclosed for registering two dimensional fluoroscopic images with a three dimensional model of a surgical tissue of interest. The method includes steps of: (a) generating, from CT or MRI data, a three dimensional model of a surgical tissue of interest; (b) obtaining at least two, two dimensional, preferably fluoroscopic, x-ray images representing at least two views of the surgical tissue of interest, the images containing radio-opaque markers for associating an image coordinate system with a surgical (robot) coordinate system; (c) detecting the presence of contours of the surgical tissue of interest in each of the at least two views; (d) deriving bundles of three dimensional lines that pass through the detected contours; and (e) interactively matching three dimensional points on three dimensional silhouette curves obtained from the three dimensional model with the bundles of three dimensional lines until the three dimensional model is registered within the surgical coordinate system to a predetermined level of accuracy. The step of iteratively matching includes steps of: defining a distance between surfaces of the model and a beam of three dimensional lines that approach the surfaces; and finding a pose of the surfaces that minimizes a distance to the lines using, preferably, a statistically robust method, thereby providing a desired registration between a surgical robot and a preoperative treatment plan.

35 Claims, 17 Drawing Sheets

U.S. PATENT DOCUMENTS

| | | |
|---|---|---|
| 5,230,623 | 7/1993 | Guthrie et al. . |
| 5,279,309 | 1/1994 | Taylor ................................. 128/782 |
| 5,299,288 | 3/1994 | Glassman et al. ..................... 395/80 |
| 5,402,801 | 4/1994 | Taylor ................................. 128/898 |
| 5,445,166 | 8/1994 | Taylor ................................. 128/897 |
| 5,553,198 | 9/1996 | Wang et al. . |
| 5,662,111 | 9/1997 | Cosman . |
| 5,682,890 | 11/1997 | Kormos et al. . |
| 5,769,078 | 6/1998 | Kliegis . |
| 5,772,594 | 6/1998 | Barrick . |
| 5,785,706 | 7/1998 | Bednarek . |
| 5,792,146 | 8/1998 | Cosman . |

OTHER PUBLICATIONS

"Accurate Calibration of Cameras and Range Imaging Sensors: the NPBS Method", G. Champleboux et al., IEEE 1992, pp. 1552–1557.

"Camera Models Based on Data from Two Calibration Planes", H.A. Martins et al., Computer Graphics And Image Processing 17, 173–180 (1981).

"Towards automatic registration between CT and X–ray images: cooperation between 3D/2D registration and 2D edge detection", Ali Hamadeh et al., pp. 39–46, Oct. 1995.

"3D–2D projective registration of free–form curves and surfaces", Jacques Feldmar et al., INRIA 1994, No. 2434, 43 pages.

"Matching 3–D Smooth Surfaces with their 2–D Projections using 3–D Distance Maps", Stephane Lavalee, et al., SPIE vol. 1570 Geometric Methods in Computer Vision (1991), pp. 322–336.

"Robust methods for estimating pose and a sensitivity analysis", Rakes Kumar, et al., pp. 1–46, Jun. 1993.

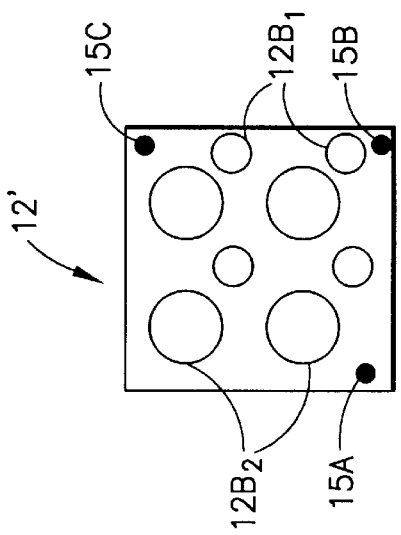
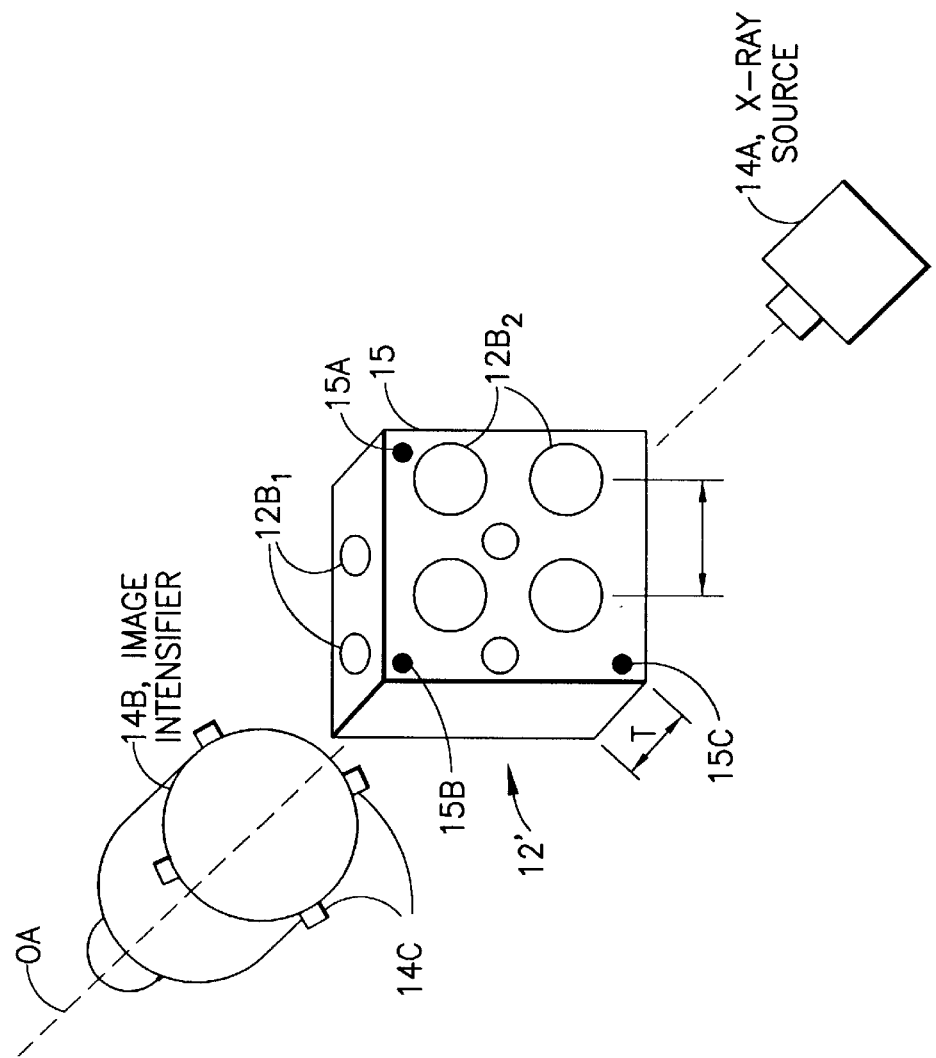

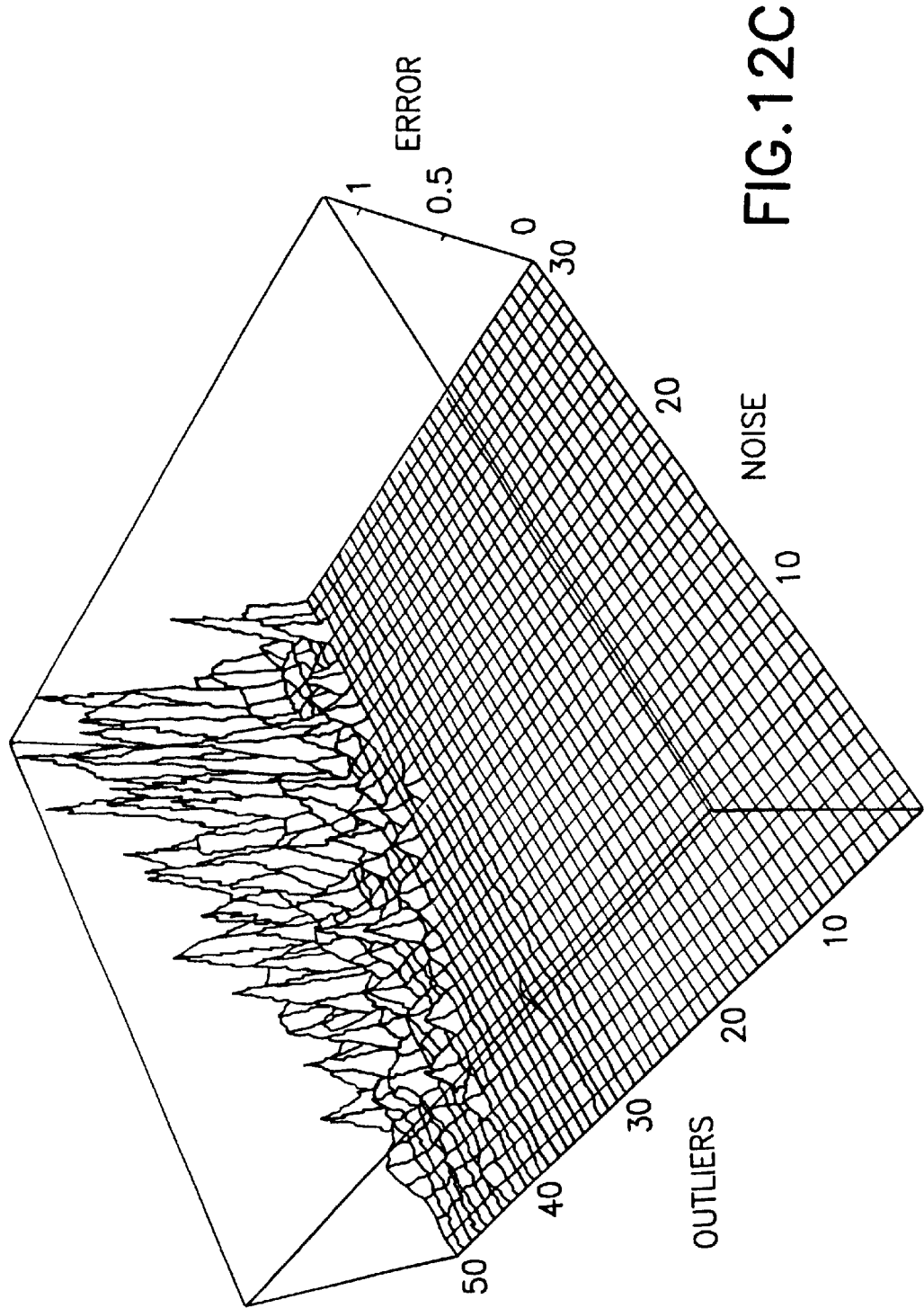

METHODS AND APPARATUS FOR REGISTERING CT-SCAN DATA TO MULTIPLE FLUOROSCOPIC IMAGES

FIELD OF THE INVENTION

This invention relates generally to robotics and medical imaging techniques and, in particular, to methods for registering a robot to a planned trajectory for assisting in surgical procedures.

BACKGROUND OF THE INVENTION

Computers are increasingly used to plan complex surgeries by analyzing preoperative Computed Tomography (CT) or Magnetic Resonance Imaging (MRI) scans of a patient. In order to execute the surgical plan, it is important to accurately align or register the three dimensional preoperative data to an actual location of the anatomical features of interest during surgery.

One conventional technique for performing this type of registration is to attach a stereo-tactic frame or fiducial markers to the patient, and to precisely locate the frame or markers both prior to and during surgery.

For example, a conventional registration protocol includes implanting three metallic markers or pins in a patient's femur, one proximally in the trochanter and two distally in the condyles, near the knee. The insertion of the pins requires minor surgery. A CT-scan image of the patient is subsequently acquired. By analyzing the CT data, the surgeon decides upon the size and location of the implant that best fits the patient's anatomy. During surgery, the metallic pins are exposed at the hip and knee. The patient's leg is attached to a surgical robot device that must then locate the exposed pins. A registration, or coordinate transformation from CT space to robot space, is computed using the locations of the three pins as a Cartesian frame. The accuracy of this registration has been measured to be better than one millimeter. However, the use of such pins as markers is not always desirable, as they may cause significant patient discomfort, and the required surgical procedure to insert and subsequently remove the pins results in inconvenience and additional cost to the patient.

An alternative technique is to perform anatomy-based registration that uses anatomical features of the patient, generally bony features, as markers for registration.

Conventional methods for anatomy-based registration of three dimensional volume data to projection data include three techniques, described by Lavallee et al. in "Matching 3-D smooth surfaces with their 2-D projections using 3-D distance maps", proceedings of Geometric Methods in Computer Vision, SPIE vol. 1570, pages 322–336, 1991; by Lee in a PhD Thesis on "Stereo Matching of Skull Landmarks", from Stanford University in 1991; and by Feldmar et al. in Technical Report No. 2434, "3D–2D projective registration of free-form curves and surfaces" from INRIA, Sophia Antipolis, 1994.

In the approach of Lavallee et al., "Matching 3-D smooth surfaces with their 2-D projections using 3-D distance maps", calibrated video images are used to register a model of a vertebra to its projections. A hierarchical volume is built that is used to query the closest point from anatomical surfaces to projection lines. Also defined is a negative distance to address the situation of lines intersecting the surface.

In the approach described by Lee, "Stereo Matching of Skull Landmarks", stereo pairs of radiographs are used to track in real time the position of a patient's skull during radiotherapy delivery. Localized bony features that are segmented from a CT-scan are employed for this purpose.

In the approach described by Feldmar et al., "3D–2D projective registration of free-form curves and surfaces", surfaces are registered to projected contours. This is accomplished by defining image-to-surface correspondences and by minimizing a least squares criterion using iterative methods. The criterion incorporates contour and surface normals. This method accommodates errors in calibration by allowing optimization of the camera parameters.

Conventional methods for performing geometric calibration of images include a two-plane method described by Martin in "Camera Models Based on Data from Two Calibration Planes", published in Computer Graphics and Image Processing, 1981, volume 17, pages 173–180, and a method described by Champleboux et al. in "Accurate Calibration of Cameras and Range Imaging Sensors: The NPBS Method" published in ICRA Conference Proceedings, 1992, pages 1552–1557.

The calibration of distortion-free radiographs was investigated by Brown, "Registration of planar film radiographs with computed tomography", in Mathematical Methods in Biomedical Image Analysis, pages 42–51, San Francisco, Calif., June 1996, IEEE.

Most of the above described techniques, with the notable exception of Lee's, uses high quality three dimensional and projection images for experiments, such as high resolution CT scans of dry bones, or simulations of radiographs using video images. However, such high quality data is typically only available in a controlled laboratory test, and is superior to the data that would normally be clinically available. For example, typical CT slices also show soft tissue, present notable artifacts, and are of wide and unequal spacing to minimize the x-ray doses delivered to the patient. A precise segmentation of such data presents a very challenging problem. Furthermore, most fluoroscopic images that are obtained with commonly available clinical devices are characterized by a narrow field of view (FOV), typically with a maximum FOV of 100 mm, and include significant noise and distortion.

As such, there exists a need to provide an improved system and method for accomplishing an anatomy-based registration of three-dimensional data (model data) obtained from a scan, such as a CT scan or an MRI scan, to two dimensional projection data, such as x-ray data, enabling the registration of a surgical robot to a preoperative treatment plan.

OBJECTS AND ADVANTAGES OF THE INVENTION

It is thus a first object and advantage of this invention to provide a system and method for anatomy based registration of a three-dimensional CT-scan to two dimensional x-ray projection data.

It is a further object and advantage of this invention to provide a system and method for anatomy based registration of a three-dimensional CT-scan to two dimensional x-ray projection data, enabling the registration of a surgical robot to a preoperative treatment plan.

A further object and advantage of this invention is to provide a method for geometrically calibrating x-ray projection images using a calibration device that includes radio-opaque markers, wherein in one embodiment the calibration device is manipulated by the robot.

Another object and advantage of this invention is to provide a method for processing a three dimensional model and a set of inverse projection three dimensional lines to reduce the complexity of the task of registering the model to the lines by making the task a succession of sub-tasks of registering points to lines.

Another object and advantage of this invention is to provide an efficient, reliable, and clinically viable method for registering a set of three dimensional points to a set of three dimensional lines.

SUMMARY OF THE INVENTION

The foregoing and other problems are overcome and the objects and advantages are realized by methods and apparatus in accordance with embodiments of this invention.

In accordance with the teachings of this invention, and in one embodiment, an image calibration device is attached to a robot end effector. A conventional fluoroscope and video image digitization system and software are used to acquire fluoroscopic images while the robot manipulates the calibration device along multiple surfaces (not necessarily planar), approximately perpendicular to a fluoroscope optical axis. A plurality of radio-opaque markers, such as small metallic spheres that are carried by the image calibration device are automatically extracted from the fluoroscopic images and labeled, using edge detection and circle finding techniques. A thin plate spline function is fitted to each two dimensional coordinate (x, y location) of the marker position data. Contours of target data are extracted from the fluoroscopic images using operator-assisted active contours software.

Next, two dimensional imager paths are delivered, such as x-ray paths, that correspond to the inverse perspective projection of the target data contours. A geometric model of the boundary of the target data is extracted from CT-scan data using the operator-assisted active contours software and also contour tiling software. X-ray paths are registered to the geometric model by specifying an initial position of the geometric model by computing silhouettes of the model and by registering the paths to points along the silhouettes. As employed herein, the term 'surface silhouettes' and the term 'surface apparent contours' have the same meaning.

Disclosed herein is a semiautomatic method for registering preoperative CT scan data to a robot used intraoperatively for, by example, Total Hip Replacement Surgery (THRP). A goal is to utilize anatomical features of the patient for registration markers.

In the preferred embodiment of this invention x-ray fluoroscopy images are used to perform the registration. A technique is disclosed for the calibration of these images with respect to the surgical robot, such that a 3-D projection line can be fully specified in robot space for each image pixel. The calibration uses the above mentioned image calibration device, embodied in a radiolucent rod with removable metallic beads, or uses a stationary calibration grid device that is interposed along the optical axis of the x-ray system, and which has points that are touched by the robot during the calibration procedure for providing a position reference.

Surface models of a tissue of surgical interest, such as the femur, are extracted from the CT-scan data. The method then defines a distance between surfaces of the model and a beam of 3-D lines, and finds a pose, that is, the 3-D position and orientation, of the surfaces that minimizes the distance to the lines using a statistically robust method, thus providing a desired registration. The registration method in accordance with this invention uses surface apparent contours to assign a positive distance to lines intersecting the surface.

BRIEF DESCRIPTION OF THE DRAWINGS

The above set forth and other features of the invention are made more apparent in the ensuing Detailed Description of the Invention when read in conjunction with the attached Drawings, wherein:

FIG. 1B is a pictorial illustration of the process for geometric calibration of fluoroscopic images using a robot manipulator and a second embodiment of the calibration device, in particular a fixed radiolucent body that contains radio-opaque markers for providing a calibration grid.

FIG. 1C is view of the grid structure of FIG. 1B looking along the optical axis (OA).

FIG. 12C is a similar graph that illustrates a maximum registration error for a presently preferred Robust method.

DETAILED DESCRIPTION OF THE INVENTION

Figure 1A:
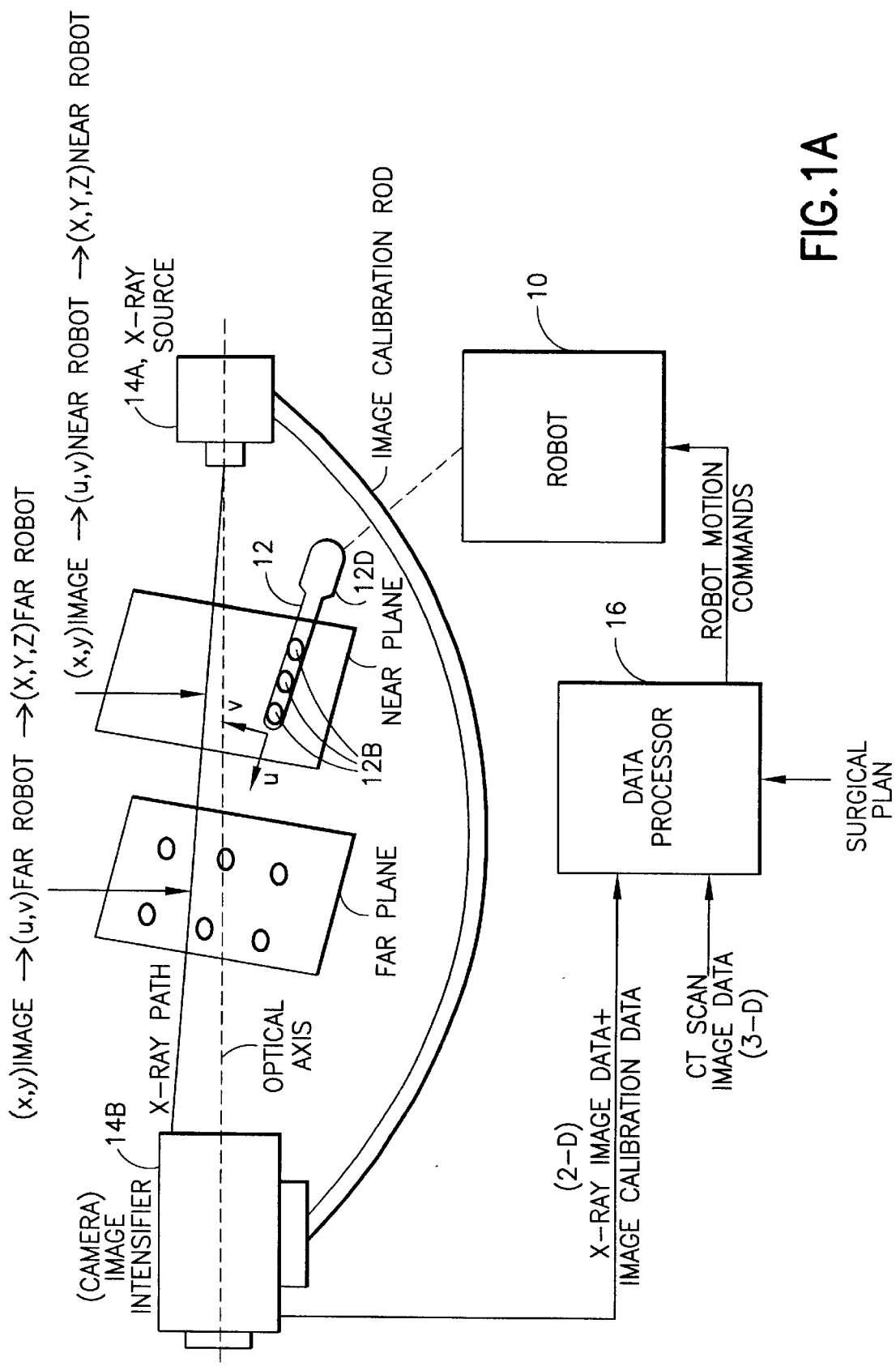
FIG. 1A is a pictorial illustration of the process for geometric calibration of fluoroscopic images using a robot manipulator and a first embodiment of a calibration device, in particular a moveable radiolucent rod that contains radio-opaque markers.
Figure 2A:
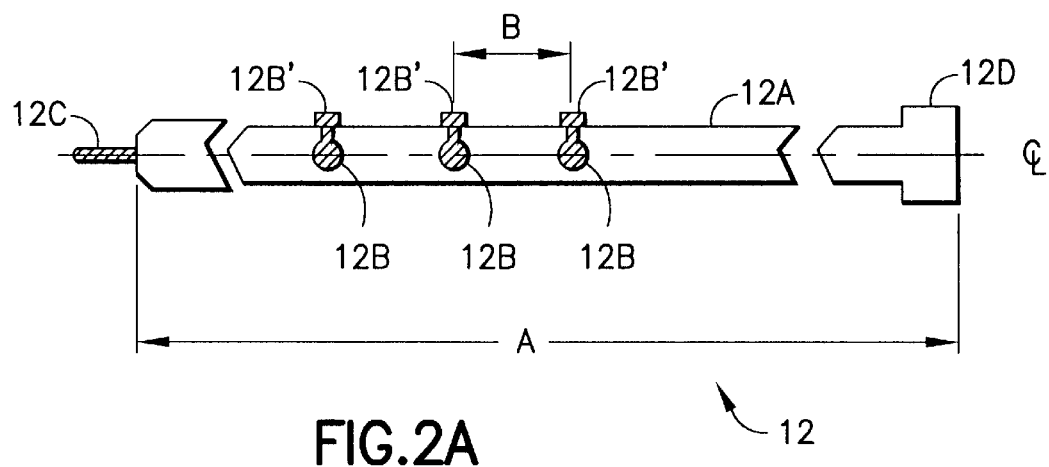
FIGS. 2A and 2B are partial cross-sectional views that illustrate the rod-shaped calibration device of FIG. 1A in greater detail.
Figure 2B:
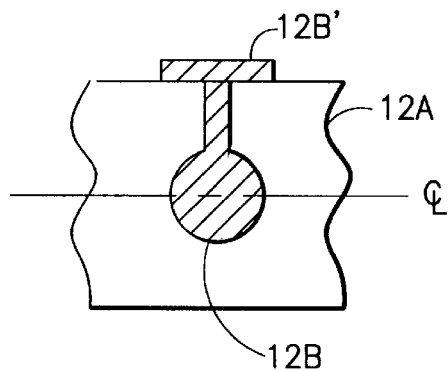

By way of introduction, and with respect to the conventional approaches described above, the teaching of this invention provides a number of novel and clinically useful advances. Referring to FIGS. 1A, 2A and 2B, the inventors disclose a novel image calibration technique that uses an image calibration device that is comprised, in a first embodiment, of a rod 12 having radio-opaque metallic beads 12B (for example 12 stainless steel beads each of 3 mm diameter spaced 10 mm apart (dimension B)) that are imbedded in a generally circular cylindrical radiolucent body 12A (e.g., plexiglass or preferably an autoclavable material such as ULTEM™) and held in place with screws 12B'. The rod 12 has an exemplary length (A) of 275 mm, a diameter of about 15 mm, and has one end 12D adapted to be fitted to the effector end of a robot 10. The rod 12 can thus be controllably positioned by the robot 10 along parallel planes that are generally perpendicular to an optical axis (OA) of a fluoroscopy system comprised of an x-ray source 14A and an image intensifier (camera) 14B. A radio-opaque probe 12C (length 15 mm) may be fitted into the opposite end of the rod 12. The probe 12C is useful for precisely corresponding the robot to the orientation and position of the rod 12, as the probe's position marks the end of the rod, and also indicates the rod's pointing direction. Each individual bead 12B is preferably removable, and can be replaced at the same location with an accuracy of one tenth of a millimeter.

In general, in this embodiment the calibration device 12 has a generally circular cylindrical rod-like shape and has the radio-opaque markers spaced apart along a longitudinal axis of the calibration device.

The image intensifier 14B and support electronics outputs 2-D x-ray image data, including the calibration data, to a data processor 16, which also receives CT or MRI scan data and a surgical plan. The data processor 16 operates on this data, in accordance with the methods described below, so as to output robot motion commands to the robot 10. In response, the robot 10 performs or assists in the performance of a surgical technique, such as accurately positioning a cutting tool to remove a portion of the femur to receive an implanted device. The robot 10, in this embodiment, also translates the calibration device 12 as described above.

The significance of the various coordinates depicted in FIG. 1A will become apparent during the ensuing discussion of the methods of this invention.

FIGS. 1B and 1C illustrate an embodiment of a second calibration device 12' in accordance with this invention. In this embodiment the image intensifier 14B is fitted with a fixation mechanism, such as flanges 14C, for holding a radiolucent (e.g., ULTEM™) calibration body 15 at the entrance aperture of the camera. In other embodiments the calibration body 15 is not attached to the image intensifier 14B, but is otherwise fixed in position such that the optical axis passes through the calibration body 15. The calibration body 15 has a total thickness T of about 200–300 mm, and a height and width (or diameter) determined by the dimensions of the entrance aperture of the image intensifier 14B. The calibration body 15 contains a plurality of metallic beads 12B (e.g., 6–12 beads in each of two planes, although only four are shown in the drawing). The beads are of two sizes. For example, a first set of smaller beads $12B_1$ have a diameter of, by example, 3 mm and are located in a first plane that is nearer to the image intensifier 14B than a second set of larger beads $12B_2$ located in a second plane that is parallel to the first plane of smaller beads. The second set of larger beads $12B_2$ have a diameter of, by example, 4 mm to 5 mm. The center-to-center spacing of the beads within each set or plane of beads is about 10 mm, and the spacing between the two sets of beads can be, by example, within a range of about 200 mm–300 mm. The relative sizes of the beads with respect to one another and with respect to the calibration body 15 are not shown to scale in FIGS. 1B and 1C. The space between the two planes of beads 12B may be empty. The calibration body 15 further comprises three calibration marks 15A, 15B and 15C which are touched by the end effector of the robot 10 during the calibration process, thereby fixing the location of the calibration body 15 and the beads, in the x-ray images, to the robot coordinate system. FIG. 1C shows a view of the calibration device 12' looking along the optical axis (OA) from the image intensifier 14C, with the calibration device rotated 180 degrees about the OA from the view shown in FIG. 1B. The effect is that the image of the beads forms a calibration grid that is superimposed on the x-ray image data that is output from the image intensifier 14B to the data processor 16. By making the beads of different sizes the two sets of beads can be distinguished from one another during a subsequently executed image edge detection and circle finding procedure. This technique is thus analogous to positioning the rod 12 in the two parallel planes, as described above. The calibration body 12 may have a monolithic construction, or may be comprised of two radiolucent frames, each containing one set of beads 12B, that are connected together. In this case, and as was noted above, an open space may exist between the two frames of beads 12B, such that the two bead planes are spaced apart by the desired distance.

A general principle of the calibration method is similar in some respects to that of a two-plane method (see, for example, H. A. Martins et al., "Camera models based on data from two calibration planes", Computer Graphics and Image Processing, 17:173–180, 1981). The method of this invention is particularly simple, and facilitates automatic feature extraction and identification.

In addition, a novel pose estimation algorithm is employed that uses surface apparent contours for determining correspondences between lines and surface points. Using the method one can adequately treat the case of lines intersecting surface triangles and thus treat the case of lines intersecting the surface. The search for correspondences uses a novel method that (experimentally) performs in constant to logarithmic time. A robust method is also used for computing the registration of points to lines, as will be described in detail below. Also, and inspired from the distal pins used clinically, this invention exploits the rigid structure of the femur by collecting images of the knee to perform the registration on the proximal femur. This use of image based registration has as one advantage that the anatomy of the knee is generally intact for patients undergoing Total Hip Replacement (THR), contrary to the proximal part. Using clinically available data, and comparing with a clinical protocol for registration, the use of the teachings of this invention present a significant advance in the clinical use of anatomy based registration.

Disclosed herein is a method for the rigid registration, i.e., without deformation, of CT data to the operating room theater based upon anatomical features. A preferred, but not limiting, context of this invention is Primary (PTHR) and Revision (RTHR) Total Hip Replacement Surgery assisted with, in a preferred embodiment, a ROBODOC™ robotic device of a type manufactured by Integrated Surgical Systems of Sacramento, Calif. Reference can also be had to P. Kazanzides et al., "An integrated system for cementless hip replacement", IEEE Engineering in Medicine and Biology Magazine, 14(3), 1995. Reference may also be had to U.S. Pat. No. 5,299,288, entitled "Image-Directed Robotic System for Precise Robotic Surgery Including Redundant Consistency Checking", by Glassman et al.; U.S. Pat. No. 5,279,309, entitled "Signalling Device and Method for Monitoring Positions in a Surgical Operation", by Taylor et al.; U.S. Pat. No. 5,402,801, entitled "System and Method for Augmentation of Surgery", by Taylor; and U.S. Pat. No. 5,445,166, entitled "System for Advising a Surgeon", by Taylor, the disclosures of which are incorporated by reference herein in their entireties for teaching suitable types of surgical robot and support systems that can be used to practice the instant invention.

In total hip arthroplasty, also referred to as PTHR, a patient's diseased or damaged hip joint is replaced with a two part implant inserted both in the acetabulum and femur.

In RTHR, a failed implant (either in the acetabulum, femur, or both) is replaced with a new implant. The purpose of the robot 10 is to accurately prepare the femoral cavity for insertion of the implant by controllably removing bony tissue to accommodate the insertion of the implant.

Figure 3:
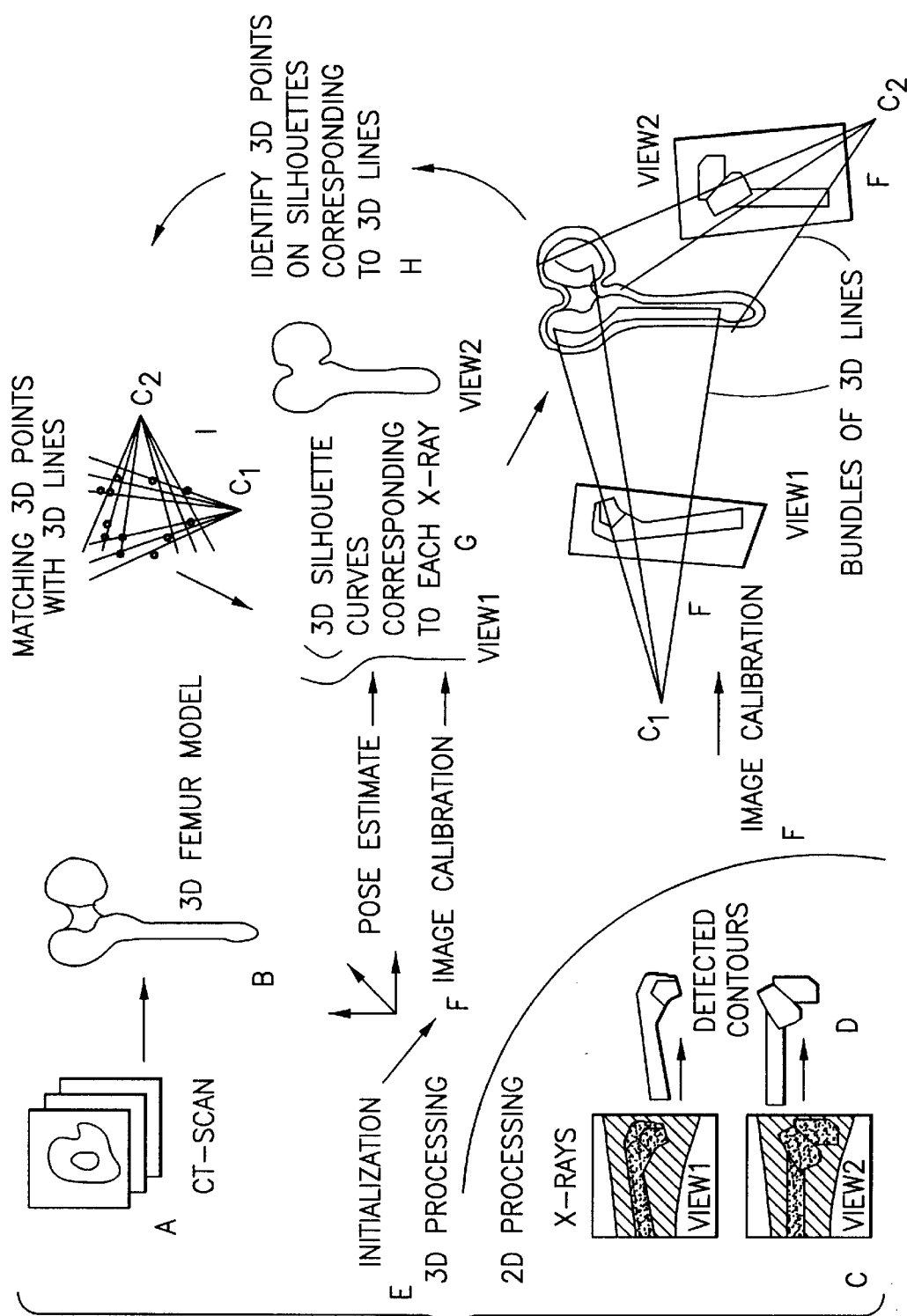
FIG. 3 is a flow chart illustrating a method for the registration of three dimensional image or surface data to projection data using the methods of this invention.

In accordance with the teachings of this invention, and referring also to FIG. 3, a method is disclosed to either eliminate entirely the use of the above described implanted pins, or to use only one proximally located pin. One significant difference with the conventional protocol is that, at most, only one pin is inserted before surgery. During the surgery the fluoroscope 14A, 14B captures radiographs of the knee and hip regions, at different angles, yielding at least two different views. In the embodiment of FIG. 1A the calibration rod 12 is inserted in the end effector of the robot 10. For each view, the rod 12 is moved by the robot 10 within two different nominally parallel planes. Each time the robot 10 moves the rod 12, a radiograph is acquired. The radiographic images of the calibration rod 12, in particular the radio-opaque beads 12B, are used to produce a calibration of each view. Alternatively, the embodiment of FIGS. 1B and 1C can be used in lieu of the rod 12. Once the images are calibrated, an extraction of the profile of the femur is made in each of the views using active contours. Using the calibration, a beam of three dimensional (3-D) lines is associated to each image profile. 3-D surface models of the bony anatomy are then extracted from the CT-scan, and an estimate is made of the pose of the surface models that minimizes a distance from the surfaces to the beam of lines. This pose, that can be constrained by the placement of one pin, provides the desired CT to robot registration. The desired goal is to obtain an accuracy of 2 mm or better for the registration.

At Step A in FIG. 3 CT-scan data is obtained, and the resulting image slices are processed at Step B to yield an accurate 3-D model of the femur (or any other tissue of surgical interest). At Step C a plurality of x-ray views (e.g., View 1, View 2) of the femur are obtained, the views including the image location calibration markers from the calibration device 12 or 12', and at Step D the x-ray views obtained at Step C are processed to detect contours. At Step E processing is initialized by the data processor 16 of FIG. 1A. At Step F images are calibrated using the process described above for producing a bundle of 3-D lines passing through the 2-D contours. At Step G pose estimation and image calaibration data are used to determine on the 3-D model various 3-D silhouette curves corresponding to each x-ray view. At Step H the method identifies 3-D points on the silhouette curves that correspond to 3-D lines, and at Step I a matching process is performed to match 3-D points with 3-D lines. The Steps G. H and I are iterated one or more times until the femur surface model data and the x-ray image data converges, resulting in a calibration of the x-ray data to the femur model.

A more detailed description of this invention is now provided.

Radiograph Acquisition and Calibration

The term "view" is used herein to mean a collection of radiographs taken in the exact same position of the patient and fluoroscope. The term "calibration" is used herein to mean a determination of the perspective camera parameters, as well as determination of, and compensation for, camera distortion. For fluoroscopic images, it has been shown that the distortion is very significant as well as position dependent, due to the interaction of a magnetic field with the electron beam within the image intensifier.

Figure 5A:
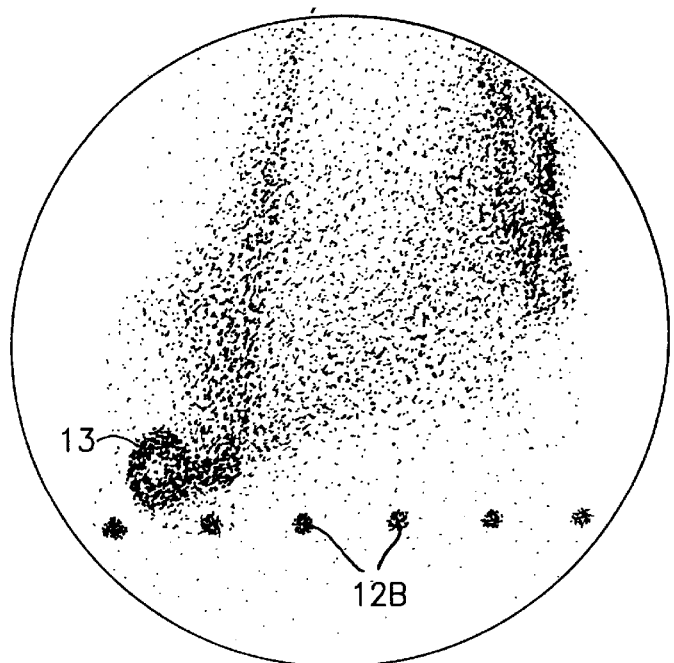
FIGS. 5A and 5B illustrate an aspect of radiographic calibration, and depict fluoroscopic images of the proximal part of the femur with the calibration rod of FIGS. 1A, 2A and 2B in two different positions.
Figure 5B:
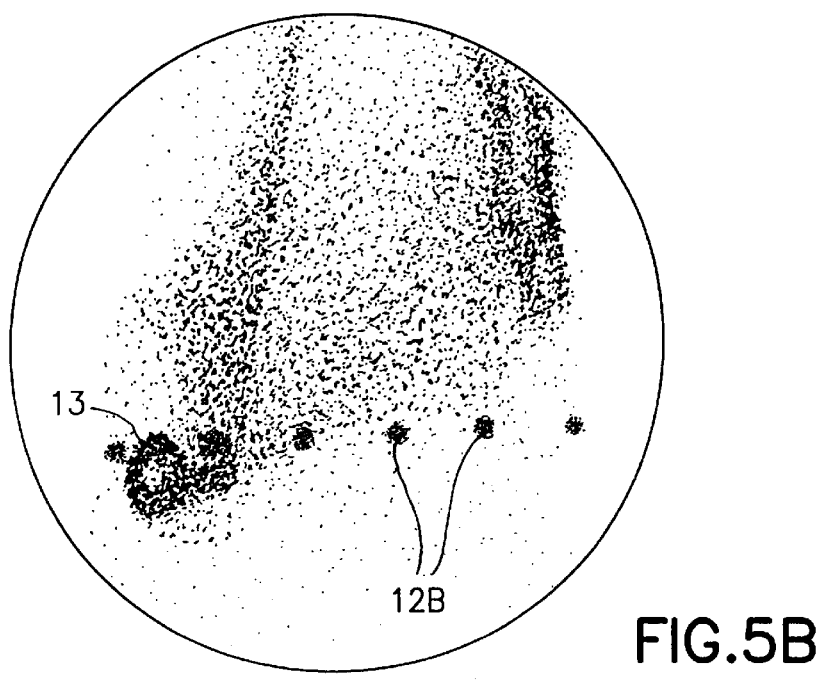

For each view, the position of the rod 12 is initialized such that an origin marker, as well as subsequent markers, can be accurately located, and such that the rod 12 appears at the far side of the image. The method then alternates between radiograph acquisition and rod translation by a vector perpendicular to the rod axis, as shown in FIGS. 5A and 5B. The same operation is repeated by moving the rod 12 along a second plane that is approximately parallel to the first plane. Finally, an image can be acquired without the rod 12 to extract occlusion-free anatomical features. In FIGS. 5A and 5B the item labelled 13 is a single pin inserted into the femur. As was noted above, the method of this invention can also operate without the insertion of the pin 13.

Figure 6A:
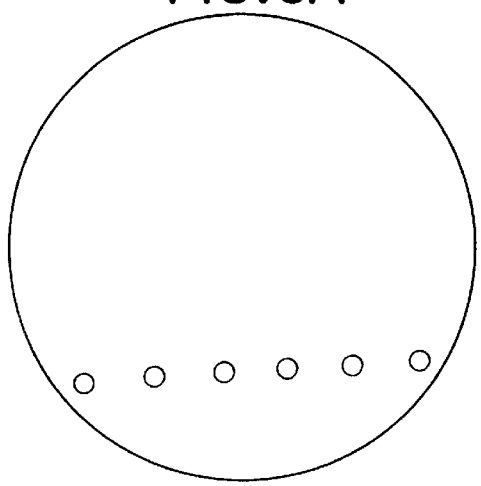
FIGS. 6A and 6B depict the automatic segmentation of the circular shapes that appear in the images of FIGS. 5A and 5B, enabling the automatic labeling of the calibration markers.
Figure 6B:
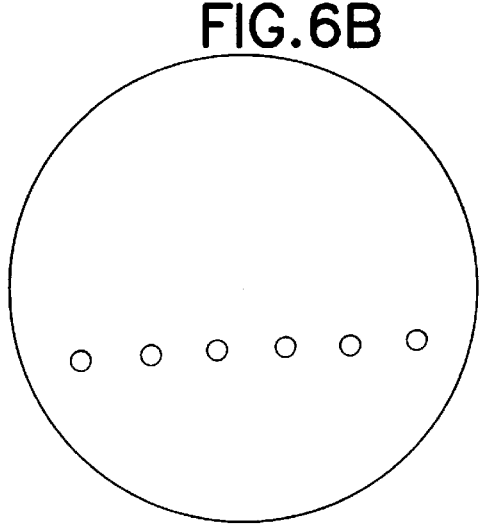

For each of the radiographs where the rod 12 shows, an edge detection technique is performed followed by a selection of the curves whose shape approximates the circle most closely. As a result only the circular markers (beads 12B) and the circle marking the field of view are retained, as shown in FIGS. 6A and 6B. This last circle has a considerably larger diameter, approximately ten times larger, than the other circles, and thus can be quickly identified and removed. The centroids of the remaining circles are then selected as the projections of markers locations.

Each marker (i.e., processed image of one of the beads 12B) is identified with coordinates (u,v) in robot space and (x,y) in image space, as detected with a segmentation algorithm. Thin plate splines are preferably used to interpolate the robot coordinates $(u_o, v_o)$, for each calibration plane, of an image point ($x_o$, $y_o$) that is not a marker. Starting with two sets of robot coordinates ($u_o$, $v_o$) and ($u_1$, $v_1$), eacg corresponding to one calibration plane, the method obtains two positions for each image point, specifying a three dimensional line referred to herein as a projection line, as any point along that line which would project to the same image pixel of the image intensifier system 14B.

The use of the thin plate splines is preferred to compensate for the image distortion, but other techniques could be used as well. Using this technique it has been found that all computed projection lines are within a distance of one millimeter from a focal point that can be determined by optimization methods, which are described in detail below. These results are in agreement with the expected extent of the x-ray source. An experiment that was performed to assess the accuracy of calibration collected an additional image of the rod 12 in arbitrary position and orientation, localized the markers on the image, computed the location of projection lines, and computed the distances of these lines to the true marker positions. The distances were found to range from 0.1 to 0.4 mm The use of thin plate spline functions for smoothly interpolating data is described by F. Bookstein, "Principal Warps: Thin-Plate Splines and the Decomposition of Deformations" in IEEE Transactions on Pattern Analysis and Machine Intelligence', vol 11, June 1989, pages 567–585.

As illustrated in FIG. 1A, the calibration rod 12 is positioned along two ruled surfaces that are referred to as the "near plane" and the "far plane". In this description it is assumed that such surfaces are planar, but the method is not restricted to planes. The "near plane" is the plane closer to the x-ray source 14A and further away from the x-ray detector (image intensifier 14B) than the far plane. For each position of the rod 12, an x-ray image is acquired with the fluoroscope.

The position of any point (X,Y,Z) on the near plane can be represented using two coordinates u and v. The coordinate v measures the position of the rod and the u coordinate is measured along the rod axis. The same applies to the far plane. Given u and v values the vector (X, Y, Z) can be computed as (rod-initial-position+u*rod-axis-vector+v*rod-motion-direction).

For each position of the rod 12 a number of markers are visible in the x-ray image that is acquired. Marker positions are digitally extracted from the images as follows. First, edge detection is performed on the images, such as by using a technique explained in Chapter 4 of Three Dimensional Computer Vision, by O. Faugeras, MIT Press, 1993. The result of edge detection is a series of oriented polygonal lines. The method retains those polygonal lines that are determined to be 1) closed, 2) of length compatible with the perimeter of a marker observed in a sample image, 3) of compactness between "low-compac" and 1.0. The low-compac is a threshold value that is typically equal to 0.9, but this value can be decreased to accept shapes that are less compact than a circle, or increased to accept only shapes that are very similar to a circle. The compactness is defined as $4\pi Area/perimeter^2$.

The compactness of a circle is exactly 1.0. For each polygonal curve, the method computes the centroid of the polygon vertices and use the centroid as a local origin. The perimeter is then computed by adding the lengths of the polygon segments. The area is then determined by computing first the areas of the triangles formed with the origin and a polygon segment and by summing such areas. Once the polygonal curves defining the markers have been extracted the method retains the (x,y) coordinate on the marker in the image. These coordinates are measured in the image coordinate system with respect to an image origin (typically, but not necessarily, the upper left corner of the image).

Figure 1D:
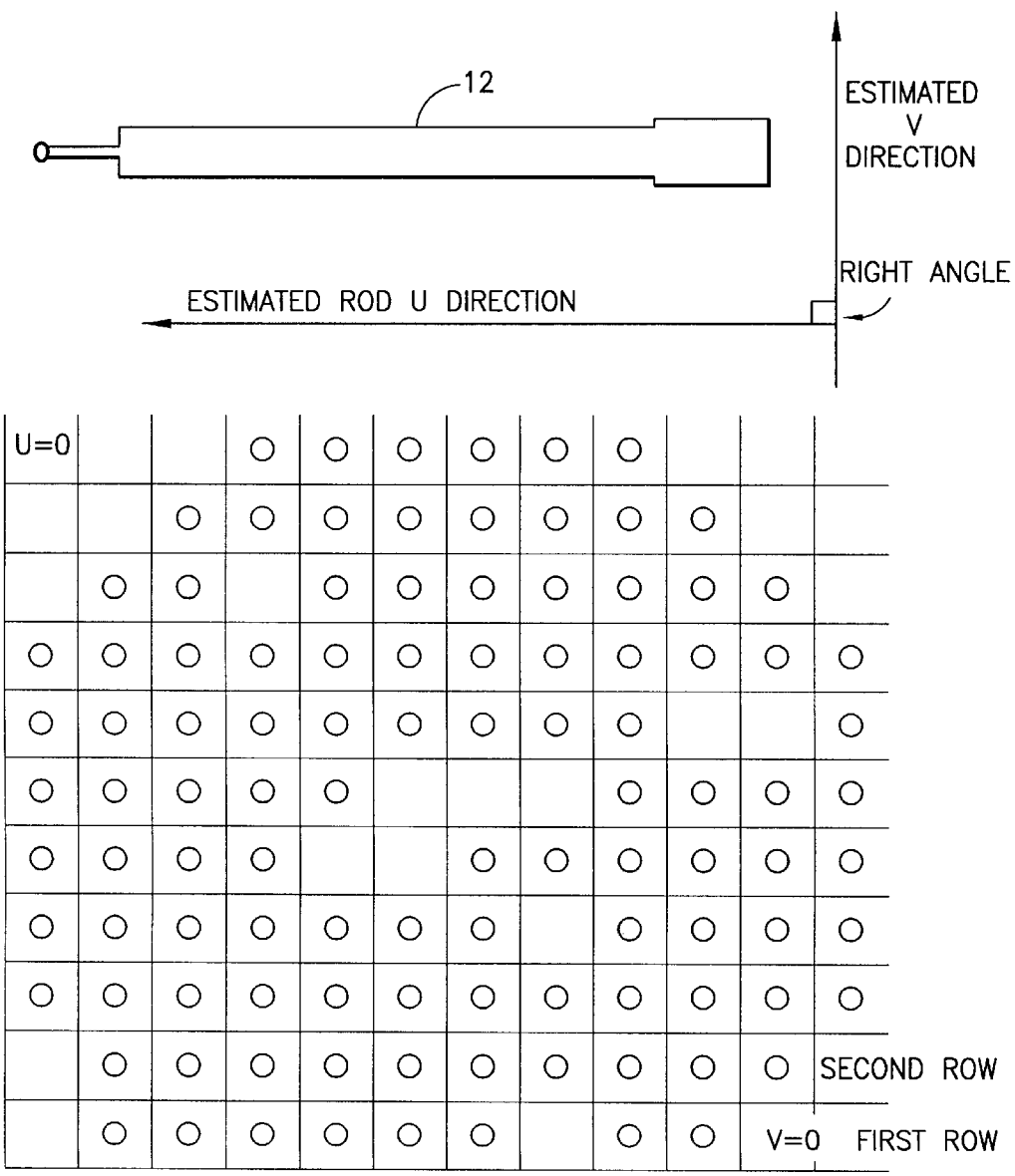
FIG. 1D is useful in understanding the description of the automatic labeling of the markers in the first embodiment of the calibration device shown in FIG. 1A.

Referring now to FIG. 1D, each marker is assigned the same v coordinate for a given image (corresponding to a given rod position). Markers are assigned a different u coordinate according to their position along the rod. The labeling, or assignment of u values to the markers, can be performed automatically once all the images have been acquired, if it can be determined on which side of the image the rod tip 12C is, and if the first marker in visible on at least one of the images. For instance, if it is determined that the origin is on the left side of the images, all the images containing the markers are superimposed, the u direction is determined by fitting a line to the set of markers corresponding to each image; the v direction is estimated as being perpendicular to the v direction. Pairwise distances between neighboring markers are computed. Based upon such estimated u and v directions of the visible marker and the pairwise average distance, the image space can be tessellated, potential integer coordinates can be computed for the markers, and converted to u and v values. At this stage an operator can be asked to verify whether the marker labeling was correct: for instance, too much image distortion could push markers outside the correct cell of the tessellation towards a neighboring cell. The leftmost marker in the u direction is assigned the u=0 value (as this is chosen to be the origin for the rod coordinate system; however the technique does not rely on this choice to apply and the definition of the origin for the rod coordinate system could be easily changed). Preceding markers on the same row are assigned lower u values according to the marker spacing on the rod: e.g. if markers are spaced 10 mm apart, the next u value will be u=10. The row of markers corresponding to the first rod position is assigned the value v=0. Subsequent rows are assigned higher v values according to the magnitude of the rod motion: e.g, if the rod is moved by 10 mm, the v value of the second row will be v=10.

This technique can be easily modified if the position of the rod tip 12C is determined to be on the right side of the images.

The role of the Thin Plate Spline functions, or TPS functions (one function is used for "u" and another function is used for "v") is to interpolate between the (u,v) values known for the markers so that any image pixel identified by its coordinates (u,v) will have u and v coordinates associated. To determine the TPS functions, the method collects all triples of values (x,y,u) for each marker and then uses, preferably, the technique described by Bookstein. The method then processes all the triples (x,y,v), and the process is repeated for the second plane. For each x-ray view, four TPS functions are determined.

Then for each image pixel, using the four TPS functions, the method determines (u,v) for the near plane, and (u,v) for the far plane. Thus two positions (Xn Yn Zn) for the near plane and (Xf Yf Zf) for the far plane are determined, thereby providing two points along a line in three dimensional space. This line in three dimensional space represents the path of the x-rays that contributed to the image pixel considered.

This technique also functions well if the near and far surfaces are not planar, meaning that the rod is allowed to perform different motions than just simple translation.

A distinction over the method disclosed by Martins et al. is that Martins uses linear or quadratic interpolation methods as opposed to using the TPS function that has the property of being the mathematical analog to a physical thin plate.

The Champleboux "NPBS' method is also used by Hamadeh et al. in "Towards Automatic Registration between CT and X-ray Images", in Medical Robotics and Computer Assisted Surgery, pages 39–46, October 1995. Significant differences between their approach and the method of this invention include the fact that they use a plate of markers as opposed to simulating a plate by translating the rod 12. In their method, the position of the plate is tracked using a system which must be installed in the operating room (OR) theater. Instead, this invention employs, for tracking the rod position, the same robotic surgical assistant that is already present in the OR theater for the intended surgery. Also, Champleboux uses an approximation to the thin plate spline functions with B-spline functions, not the thin plate spline functions employed in this invention.

Differences with the Potamianos et al. method described in "Intra-Operative Registration for Percutanecus Surgery" in Medical Robotics and Computer Assisted Surgery, pages 156–164, October 1995 include the fact that the markers they use for image calibration do not cover the entire image. In their method, the distance between the planes is 30 mm or less. Instead, it is preferred in this invention to use distances between planes starting from about 100 mm. Experiments have shown that smaller inter-plane distances result in higher calibration errors.

Further advantages of the use of the calibration rod 12 compared with the conventional techniques are as follows. First, the use of the rod 12 allows one to simulate a calibration grid with all the advantages of the grid, e.g., equal spacing of markers and regular coverage of the images, and none of its inconveniences, e.g., calibration of the grid orientation and error prone detection and identification of the markers. The use of the rod 12 thus enables one to simply and automatically identify each visible marker, as well as markers that disappear at the image border. Second, the rod 12 is more versatile than a grid, as all of the following choices can be made without a tedious and redundant alteration of the entire grid: individual markers can be removed; the spacing can be doubled or tripled; and the origin can be translated.

Alternatively, the fixed grid embodiment 12' of FIGS. 1B and 1C has also been found to provide satisfactory results, and furthermore generally requires that fewer x-ray exposures be made of the patient than when using the rod 12.

Figure 7A:
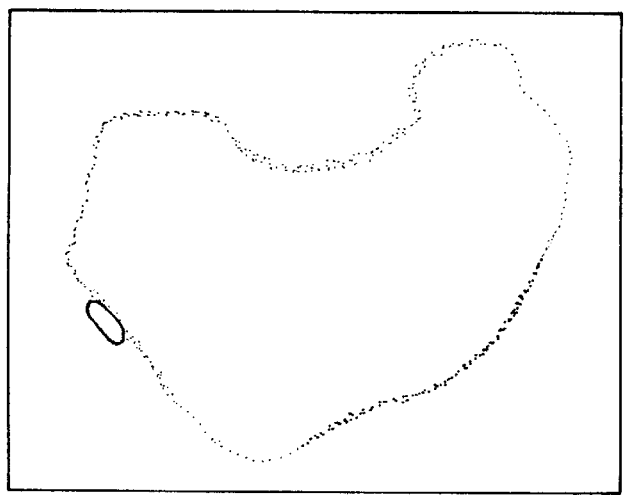
FIGS. 7A and 7B depict CT segmentation, and show a slice of the distal femur with artifacts and poor contrast (FIG. 7A) and after segmentation to yield a closed outline (FIG. 7B).
Figure 7B:
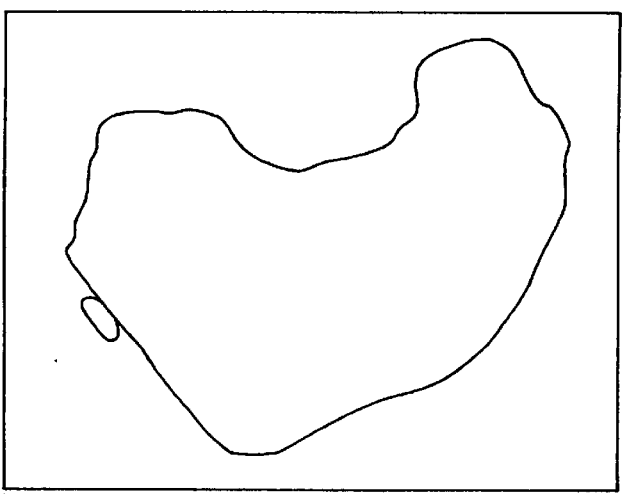

In order to extract the profiles of the bone from the radiographs, and extending a technique described by Kass et al. "Snakes: Active contour models", International Conference on Computer Vision, pages 259–268, London, June 1987, IEEE, the inventors employ a segmentation tool using a deformable model, attracted with a smoothed image gradient. A result of the use of the tool is shown in FIGS. 7A and 7B.

Segmentation of Bony Anatomy from Computed Tomography Data

A surface model is extracted from the CT-scan using a semiautomatic method. In a test CT scan, the slice spacing was found to vary widely, from 1 to 3 to 6 and finally to 120 mm. Such a variation can be expected in practice so as to maximize the detail in the critical areas while limiting the x-ray dosage. As such, iso-surface algorithms for surface extraction can be effectively ruled out, since they suffer from poor contour definition at the slice level and poor surface tiling between contours.

Instead, the following algorithm is preferred: for each slice, use an active contour model to detect the contour of the bone, as was previously done for radiographs. The result is shown in FIG. 7B. Contours are approximated to within 0.1 to 0.3 millimeters and are tiled together in an optimal fashion, such that the average triangle compactness is maximum. Triangle compactness is defined herein as a ratio: (4*sqrt 3*area of the triangle) divided by the sum of the squares of the lengths of the sides of the triangle. The optimum triangulation can be obtained using dynamic programming, and is thus computationally affordable. The resulting surface is an oriented manifold with, typically, two boundaries. The contours forming the surface as well as their level of detail are gathered in a script file, that completely determines the surface. The script file can be easily edited for examining various levels of details, or adding or omitting particular slices.

Figure 8:
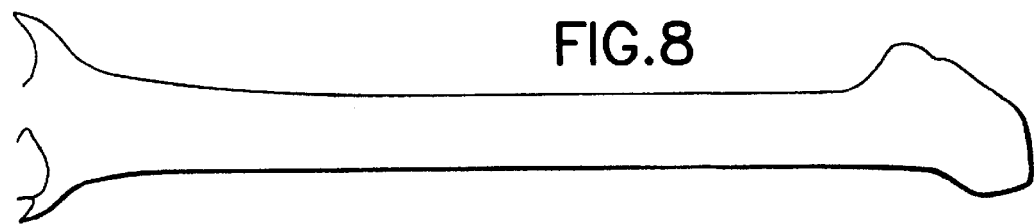
FIG. 8 is an exemplary surface model of the femur, obtained from CT-data, after tiling of the contours.

The resulting surface is then approximated with a tolerance of 0.3 mm using, in a preferred embodiment, a method described by Andre P. Gueziec, "Surface simplification with variable tolerance", MRCASII, pages 132–139, Baltimore, Md., November 1995. The final surface is shown in FIG. 8. Note that both the proximal and distal regions are incomplete, and that there is a gap of 120 mm between two slices situated distally. The final surface of the femur model contains 3,460 triangles, which is considered very compact.

A more detailed description is now provided of a presently preferred method for building a 3-D model of the femur from a set of 2D Slices of Computed Tomography (CT) image data.

In order to limit the x-ray dose delivered to the patient, CT data that is clinically available for pre-operative planning of Total Hip Replacement generally has the following characteristics. First, the spacing between consecutive slices of data is generally wide (several millimeters, whereas the spacing between image pixels in a given slice is generally below one millimeter). Second, the spacing between consecutive slice is generally uneven. In one particular protocol used for robotically-assisted interventions the slice spacing is of one millimeter in the vicinity of the metallic markers used for registration, and of six millimeters up to as much as 120 mm along the shaft of the bone, where no data is actually required. In such conditions, the resolution within a slice is much larger than the resolution along the bone axis (which is the direction aligned with the CT scanner axis). It is thus difficult to build an accurate three dimensional model of the femur that is consistent across slices.

Figure 15:
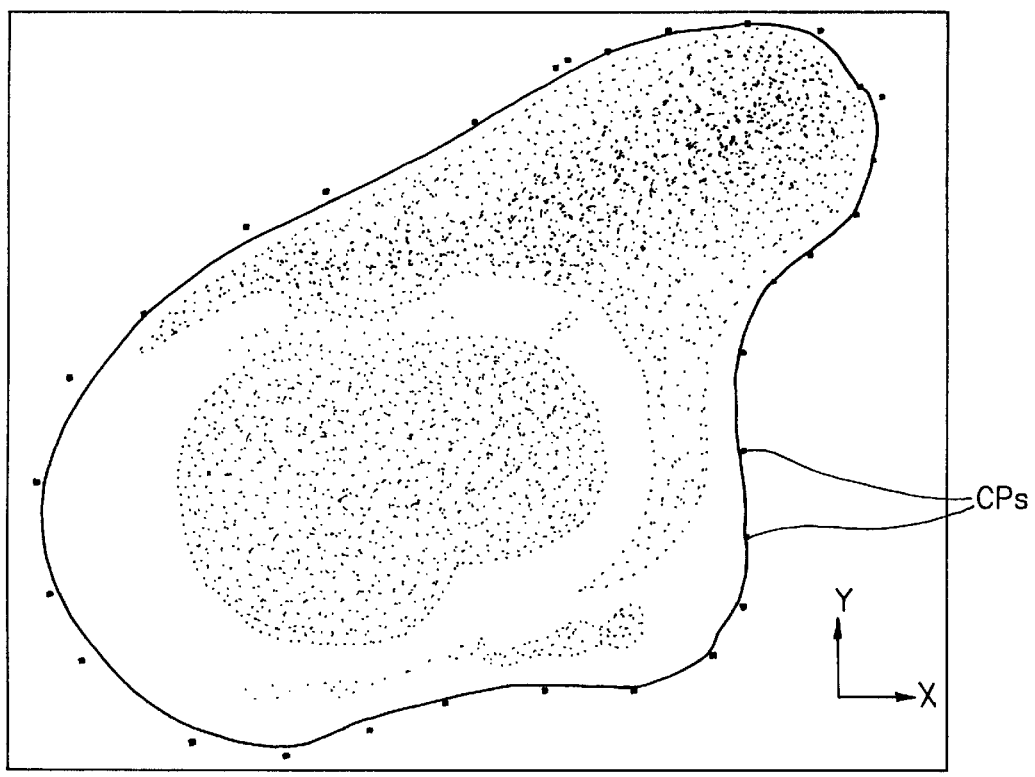
FIG. 15 depicts a display screen content during an exemplary session with a software tool used for implementing active contours.

A preferred method for building the model entails the following steps. In a first step, active contour software is used to extract the outer contours of the bone for each slice of CT data. Active contours are described in Kass, Witkin and Terzopoulos's "Snakes: Active Contour Models", in proceedings of the First International Conference on Computer Vision, 1987. In this technique, and referring to FIG. 15, an operator selects a number of control points (CPs) by "pointing and clicking" inside the CT image in the vicinity of the structures of interest. The system then constructs a polygonal curve linking the control points, and then modifies the polygonal curve to minimize an expression combining a measure of curve length, a measure of average curvature of the curve, a measure of an image potential average curvature of the curve, and a measure of an image potential. Generally, and also in the presently preferred method, the potential equals the squared norm of the image gradient. If I(x,y) is the image intensity of a pixel of location (x,y), the image gradient grad (I) is a vector whose first coordinate is the derivative of I with respect to x, and whose second coordinate is the derivative of I with respect to y. After application of the active contour technique for each slice, there is obtained one or several polygonal curves representing the contours(s) of the bone.

In a second step, the method replaces the polygonal curves with approximating polygonal curves containing fewer vertices, such that the approximating polygonal curves do not deviate from the original polygonal curves by more than a pre-specified threshold (e.g., 0.3 millimeters). Each polygonal curve is represented using an ordered array of vertices, and each vertex is indexed with its position in the array. For each polygonal curve, the following process is iterated until the maximum deviation threshold is respected. First compute the maximum deviation between any vertex and the line segment obtained by joining the last vertex with the first vertex. If the maximum deviation computed is larger than the threshold, split the ordered array of vertices into two arrays of equal size (if the number of vertices is even, the first array contains one more vertex than the second array), and then consider the two polygonal curves defined with the resulting array.

In a third step the method builds a surface model made of triangles and that contains every vertex and every edge of the approximating polygonal curves. This third step examines in turn each pair of consecutive slices and builds a surface slab that contains the approximating polygonal curves extracted from both slices.

For the case where there is one curve in the first slice and one curve in the second slice, the method proceeds by using known "dynamic programming" methods described, for example, in Cormen, Leicerson, and Rivest's "Introduction to Algorithms", MIT Press, 1994, to determine a set of triangles. The set of triangles are determined such that each triangle has at least two vertices in different curves, and the sum of triangle compactnesses, as defined above, is minimum among all possible formation of triangles.

In a fourth step the surface slabs built in the third step are combined to form a surface by removing duplicate references to vertices belonging to polygonal curves shared by any two slabs.

In a fifth and last step, the surface resulting from the fourth step is approximated by a surface containing fewer triangles using, for example, the technique described in commonly Assigned U.S. patent application entitled "Surface Simplification Preserving a Solid Volume and Respecting Distance Tolerances", Ser. No. 08/742,641, filed Nov. 1, 1996, by A. Gueziec, and also in the above referenced publication by Andre P. Gueziec, "Surface simplification with variable tolerance", MRCASII, pages 132–139, Baltimore, Md, November 1995. Distance tolerances are specified by an operator. In a typical session, a single global tolerance of 0.2 mm was employed, thus bounding the maximum deviation from the points collected using active contours by 0.2+0.3=0.5 mm.

Registration of Computed Tomography Data with Radiographs

The principle underlying the method is to iterate on the following operations: Determine for each projection line a correspondent on the surface of the model. Using, preferably, the robust algorithm described in detail below, the method determines the rotation and translation that minimizes the sum of distances from the lines to their point correspondents on the surface, and applies the transformation obtained to the surface. The method can use one or more views. The following description is made in the context of two views, although this is not a limitation on the practice of this invention.

As observed in an article by Feldmar et al., "3D-2D projective registration of free-form curves and surfaces", Technical Report 2434, INRIA, Sophia-Antipolis, France, 1994, a variation of this algorithm, that chooses new correspondents only if their distance to the line is smaller than the current distance, can be easily proven to be convergent. However, such an algorithm may not be optimal, as there are some situations when distances must increase to step out of a local minimum.

One difficulty when defining the distance of a line to a surface is to treat the case of a line intersecting the surface in potentially many locations. Any such intersection could be automatically flagged as a closest surface point to the line, with a zero distance. Ideally, after registration the lines should be tangent to the surface rather than intersecting it.

The presently preferred embodiment of this invention uses surface apparent contours, which are defined as the boundaries between visible and invisible surface triangles, whereby a visible triangle is such that a ray cast from the focal point of the lines to the triangle centroid will make an obtuse angle with the triangle normal direction. The surface apparent contours project onto the surface profile in the radiograph, and can be constructed as a set of closed, oriented, non-planar polygonal curves. For their construction, the preferred algorithm uses the surface orientation, and the focal point of the lines is determined during calibration. The data structure encodes the connectivity of the apparent contours and serves to easily prune the shortest ones considered as noise.

Line to surface correspondences are searched for on the apparent contour only. For each projection line, the method computes the closest point on the apparent contour using a hierarchical decomposition of the contours. This method can compute a closest point with a constant or logarithmic complexity in terms of the number of vertices of the polygons, even after incorporating any required preprocessing time. The worst case, obtained for particular input lines and polygonal curves, is a linear complexity, which is the complexity of linear probing.

The pose estimation may be constrained such that the transformed location of one point, the pin 13 (see FIGS. 5A and 5B), is fixed, yielding a rotation only. The difference with the algorithm described below is that one can optimize solely the parameters of the rotation, which is less computationally expensive.

Figures 9A, 9B:
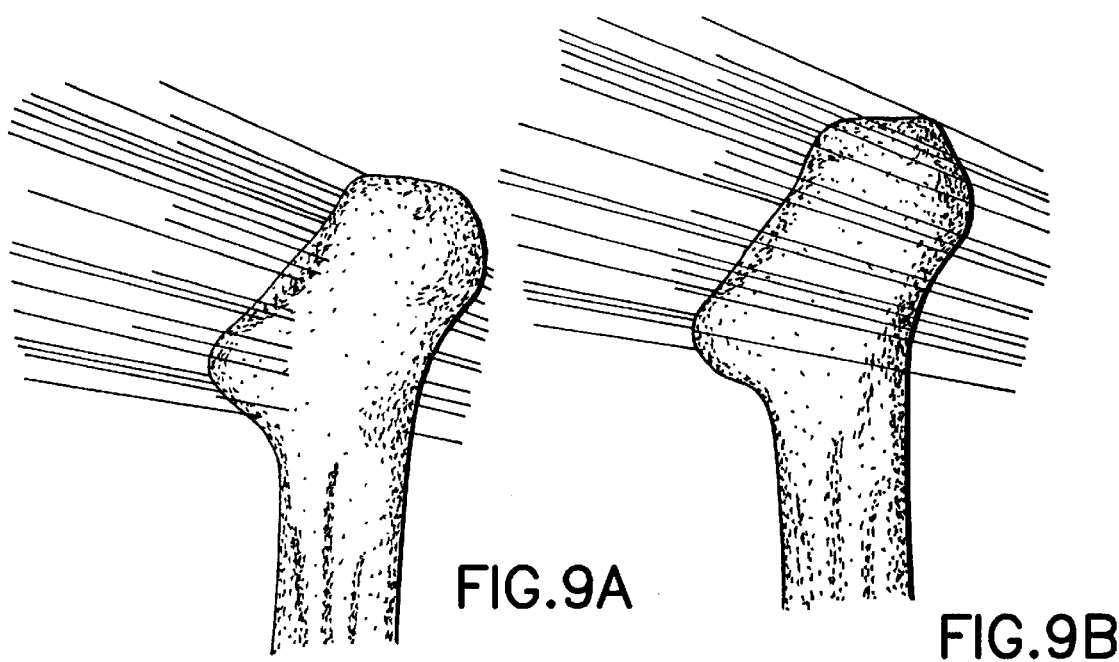
FIGS. 9A and 9B illustrate the registration of lines with surfaces, and provide a detail of the proximal part of the femur before (FIG. 9A) and after (FIG. 9B) registration.
Figure 10:
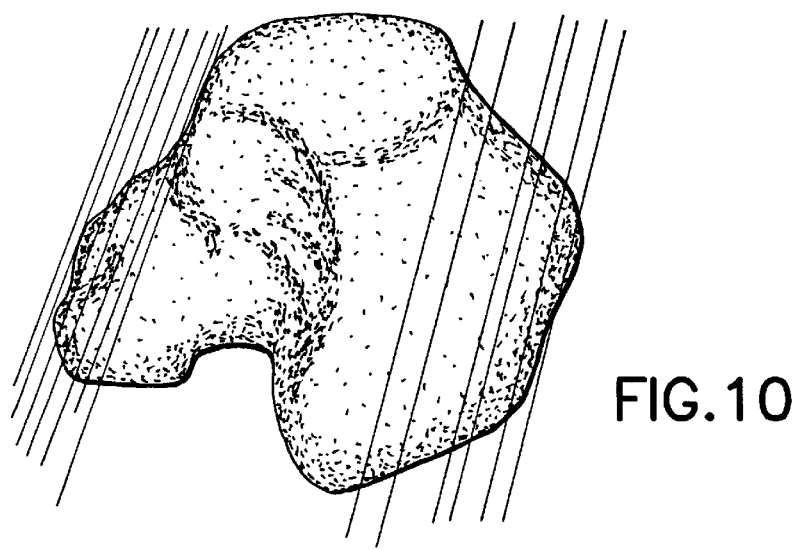
FIG. 10 shows a detail of the distal femur end after registration.

The complete registration process was found to execute in less than 6 seconds on a RS6000 Model 58K workstation. This timing incorporates the preparation of the graphics files shown in FIGS. 9A, 9B and 10. When fixing the location of the proximal pin, errors of 1.70 and 2.36 mm, respectively, were measured at the two distal pins, starting with two different initial positions of the surface.

The foregoing description has described a method that allows accuracy comparable to the three implanted pin approach, with but a single pin, using two fluoroscopic views of the bone for registration. The use of the remaining pin may be eliminated by using more fluoroscopic views, or by acquiring more computed tomography data, or by acquiring CT data with more contrast.

By example, in a subsequent experiment involving four views, two proximally separated with an angle of 60 degrees and two distally separated with an angle of 20 degrees, a satisfactory registration was obtained without the use of the single implanted pin 13.

In general, it is noted that a minimum degree of rotation between two 2-D views taken by the fluoroscopic instrument is preferably about 20 degrees. This amount of angular separation between views has been found to provide adequate results when the views are further processed as described above.

The presently preferred method to perform the registration of computed tomography data with radiographs is now described in greater detail. As employed herein a radiograph can be a fluoroscopic image, a (digitized) film x-ray image, a digital x-ray image, or any technique suitable for obtaining a two dimensional image of an internal structure of interest.

Three distinct methods are described below, specifically "LM", "Linear" and "Robust" methods, for registering 3-D points to 3-D lines, that is, finding an optimal rotation and translation that will minimize a measure of the distance between each point and a corresponding line. It is assumed that the number of points and lines is the same and the correspondence between points and lines is known. The minimum number of pairs of points is three except for the LM method for which it is six.

The problem of estimating the pose of 3-D anatomical surface models and images in one or several projective 2-D images has been described above. Another application is the superimposition of 3-D models on 2-D images to achieve realistic texture mapping to the models. These applications imply that the images have been calibrated, such that a projective line can be drawn starting at each image pixel, connecting the pixel to a perspective center, or to infinity in the case of orthographic, or parallel projection. In the case of perspective projection, the focal length and image center are assumed to be known.

The pose estimation uses the following two steps. In the first step, points are collected in 2-D together with their corresponding 3-D point. In the second step, the 3-D points are registered to the 3-D projective lines originating at the 2-D points, using one of the three methods described below. It should be noted that the lines need not have a point in common for the method to operate. In fact, the method is adapted to finding a solution for data collected in several projective views simultaneously, and to handling parallel lines that occur in orthographic projection. The process of collecting points can be performed either manually or automatically. Separating the point matching process from the numerical calculations of pose estimation has several advantages. These advantages include an ability to validate each process separately, and an ability to compensate manually for the spurious matches that are hypothesized automatically.

Each registration method presented below attempts to minimize a sum of positive measures of the Euclidean distance between a point and its corresponding line. The first two methods, LM or non-linear Levenberg Marquardt minimizer, and Linear or linearization followed by constrained minimization, use the sum of squared distances. The Robust, or the statistically robust minimizer, weights each squared distance in the sum with a function that favors distances similar to the median of the distances. All three methods are iterative minimizers of the objective function. In order to represent the 3-D rotation it is preferred to use the Cayley parametrization, because of the simplicity with which one can derive a linearization and the facilitation of the determination of the rotation parameters for rotations of small size. Also, better computational and numerical properties exist because sine and cosine functions are avoided.

To explain these methods a set of test data is generated to comprise a set of points and a bundle of lines. The maximum angle between the lines is comparable to the angle that one would observe when imaging an object using x-ray equipment. Some of the points are corrupted with white noise, and progressive increase is made in the number of corrupted points as well as the magnitude of the noise. The LM and Linear methods typically tolerate noise that does not exceed about 10% of the diameter of the cloud of data points, as well as noise of higher magnitude, provided that less than about 5% to 10% of the points are corrupted. The Robust method tolerates up to 40% of outliers at all noise levels.

It is first noted that Kumar et al., "Robust methods for estimating pose and a sensitivity analysis", CVGIP-IU, 60(3):313–342, 1994, have analyzed different formulations for the pose estimation problem and have provided a sensitivity analysis to the calibration parameters. These authors assume that the projection model is the perspective model and derive equations for line tokens correspondences. They provide several robust methods to weight out outliers. In addition, there is a large body of literature on the problem of pose estimation using points or line tokens or a more complex representation of shape. Reference in this regard can be had to Haralick et al., "Pose estimation from corresponding point data", IEEE Transactions on Systems, Man and Cybernetics", 19(6):1426–1446, November/December 1989, and the bibliography of this publication.

In accordance with the teachings of this invention a comparison is made of the nonlinear minimization to the iterative linearization in the context of radiographic applications. The method assumes that the imagery is calibrated, but does not rely on a perspective projection. Parallel projections or projections for which there are several centers of perspective, such as the scout views generated by CT scanners, are treated using the same formalism. The equations do not change if several views are used simultaneously to determine the pose, assuming the views are co-registered.

A further description is now made of presently preferred techniques for registering a 3-D surface model to bundles of lines using surface apparent contours.

After image calibration, an active contour model is used to define various contours on the x-rays that correspond to projected contours of the bone. "Internal contours" are used as well, since x-rays enable one to visualize opaque objects as being transparent.

The following method is used to register the 3-D surface model extracted from the CT-scan data to one or several bundles of lines defining x-ray paths, that were computed after image calibration as described above.

In a first stage, an initial position and orientation of the 3-D surface model is specified. All proposed solutions preferably involve a human operator. A first solution for specifying the initial position and orientation of the surface model is to specify the coordinates of the translation and the rotation angles (or the rotation matrix). A second solution is to identify three or more points on the surface model, to identify the corresponding pixels on one or on several x-ray views, to compute the x-ray paths corresponding to such pixels and to use the preferred lines to points registration algorithm described in this patent application to compute an initial translation and rotation of the 3-D surface model.

Next a method is performed for computing centers of perspective, as follows.

In a second stage, for each x-ray view, the method determines a bundle of x-ray paths. The x-ray paths may correspond to pixels that contour the bone, or to a set of equally spaced pixels. Using the lines to points registration algorithm, the method computes a potential location for the intersection of all the lines in the bundle, by minimizing the distance of one unknown point to the set of all lines in the bundle. The potential location of the intersection is referred to as the x-ray view center of perspective.

In a third stage, for each x-ray view, the method defines a set of pixels that correspond to contours of the bone. A preferred method uses active contours that are described in detail elsewhere in this present patent application. Another method applies an edge detector as explained in Chapter 4 of "Three Dimensional Computer Vision", by O. Faugeras, MIT Press, 1993. Other suitable methods described in standard textbooks on image processing and computer vision can be applied as well.

Starting with said set of pixels, the method defines a bundle of lines in 3-D of the x-ray paths corresponding to the pixels.

In the fourth stage, and for each x-ray view given the current position and orientation of the 3-D surface model and given the position of the image center of perspective, a set of surface apparent contours are computed. A surface is composed of vertices, triangles and edges. Given the position of the image center of perspective, it is determined for each triangle whether the triangle normal (or normal to the plane sustaining the triangle, such that the normal direction points towards the viewer if the triangle vertices are visited in a counter-clockwise order) makes an acute or obtuse angle with the viewing direction.

The viewing direction is defined as the vector originating from the center of perspective to the triangle centroid. The angle is acute if the scalar product between the viewing direction and the triangle normal is positive and obtuse if the scalar product is strictly negative. If the angle is obtuse, the triangle is said to be visible and invisible otherwise.

Figure 16:
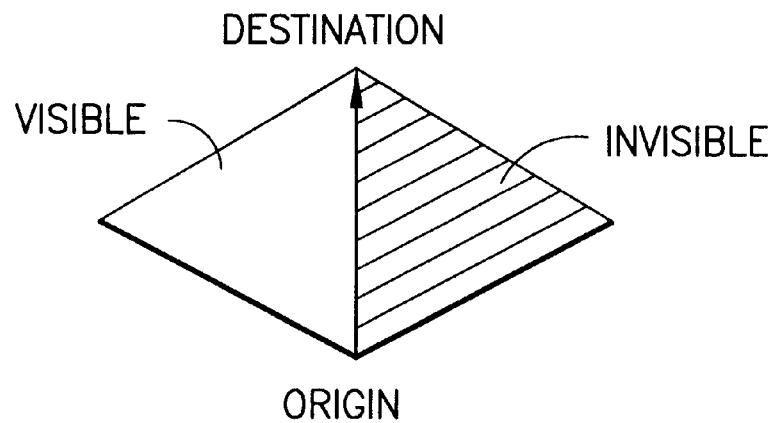
FIGS. 16 and 17 are useful in explaining the edges of apparent contours and the completing of apparent contours, respectively.
Figure 17:
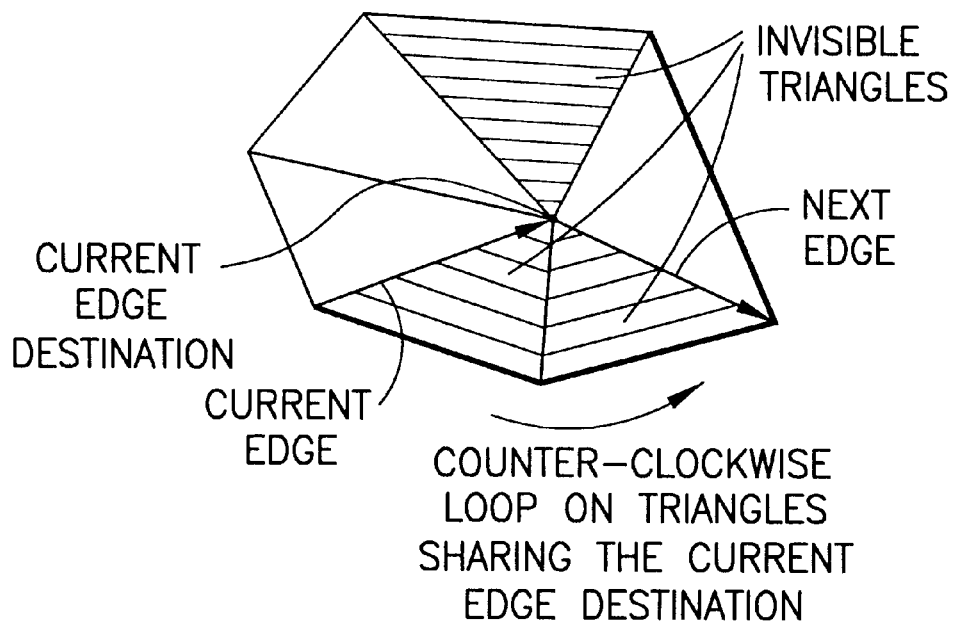

Referring also too FIGS. 16 and 17, surface apparent contours are a subset of surface edges, such that the triangle on one side of the edge is visible and the triangle on the other side of the edge is invisible. The apparent contours are such that the edges are linked to form (non-planar) closed polygonal curves in three dimensions.

To build the apparent contours, the method first identifies all edges belonging to any apparent contours using the criterion defined above, and adds such edges to a list. The edges are oriented such that the visible triangle is on the left side of the edge, as shown in FIG. 16, thus defining an edge origin and an edge destination. The method then iterates on the following process.

Step 1: Take the first edge in the list; create a new apparent contour starting with that edge; and complete the apparent contour containing that edge as follows.

Step 2: Visit the destination of the current edge and determine a next edge as shown in FIG. 17: rotate on the star of the destination vertex in a counter-clockwise fashion and determine the first edge that belongs to the list of apparent contour edges (the star of a vertex is the set of all triangles sharing that vertex).

Then re-apply Step 2 until the next edge is the same as the first edge that was processed for that contour in Step 1.

Step 3: Next remove all of the edges forming that contour from the list of apparent contour edges.

Then re-apply Steps 1 to 3 until the list of apparent contour edges becomes empty.

The fifth stage includes a method for finding the closest point on the apparent contour. This method first considers each bundle of lines in turn (there is one bundle of lines associated to each view), and for each line in the bundle, associates a point on one of the apparent contours corresponding to that view. To associate a point to the line, first compute the closest point from the line in all apparent contours in a Step A and, once all the closest points have been determined, in a Step B select a particular apparent contour and the corresponding closest point.

Figure 18:
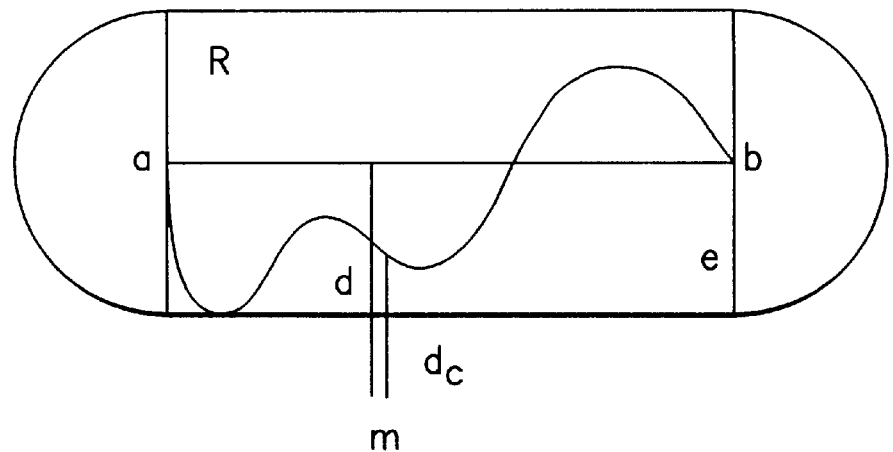
FIG. 18 is also useful in the explanation of apparent contours, and shows a case where if a point m is at a distance d from a segment ab, then the distance to a curve $d_c$ follows the relation: $d-e \leq d_c \leq d+e$, in all cases, even if m projects on either endpoint a or b of the segment.

Step A uses the hierarchical decomposition of the polygonal contours that was described elsewhere in the present patent application. First start with the first segment and compute a distance d. As shown in FIG. 18, consider the interval [d−e, d+e], with e being the maximum deviation attached to the segment. Then add the interval to a priority queue indexed with d−e. Priority queues are discussed in many textbooks on algorithms, such as Cormen, Leiserson and Rivest's "Introduction to Algorithms", MIT Press, 1994. The method then loops on the operation of taking the interval with the lowest index in the priority queue, of splitting the segment corresponding to the interval according to the information in the hierarchical decomposition of the polygonal curve, and of computing distances to both segments obtained. The looping process is terminated when it is determined that the interval with the lowest index in the priority queue [d1−e1, d1+e1] (Interval 1 corresponding to Segment 1) has an empty intersection with the next interval in the priority queue [d2−e2, d2+e2] (Interval 2, corresponding to Segment 2), meaning that d1+e1<d2−e2. The record the point q on Segment 1 that is closest to the line. Next define r=(d2−e2−e1+e1)/2, and then record the point p on the line that is closest to q.

When computing the closest point to the same polygonal curve from a second line, the method first computes the distance from the second line to the point p. If that distance is less than r then the closest point is directly searched for inside Segment 1.

It has been determined experimentally that the average complexity of determining the closest point using this method is proportional to log(n), where n is the number of vertices in the polygonal curve.

Figure 19:
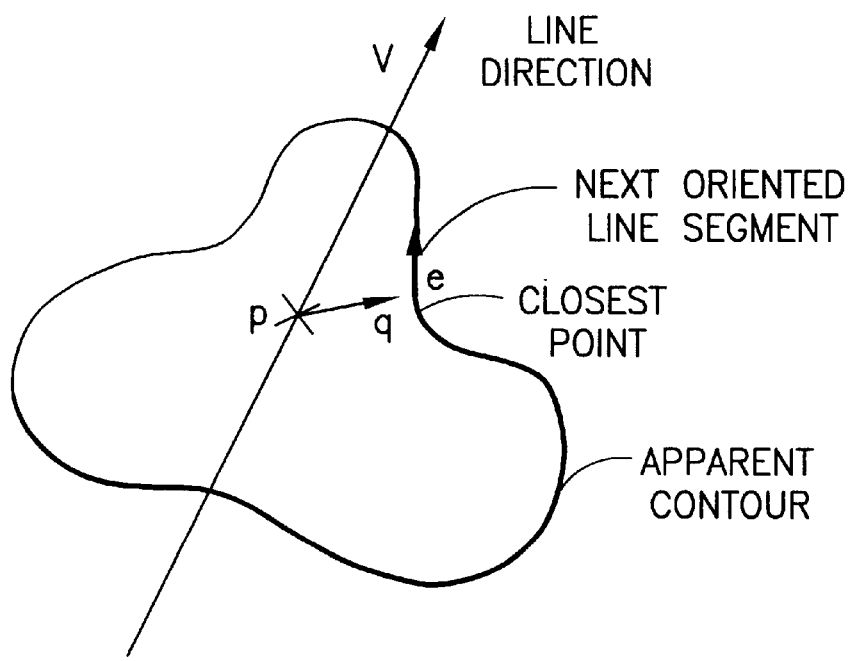
FIG. 19 graphically illustrates a construction used for determining if a particular line pierces an apparent contour.

In Step B, once all the closest points from a line to all the apparent contours have been determined according to Step A, the method first determines if the line "pierces" the apparent contour or does not pierce the apparent contour. As shown in FIG. 19, it is determined that the line pierces the apparent contour if the vector p−>q pointing perpendicular from the line at p to the closest point q on the apparent contour, the oriented edge e starting from the closest point and the line direction v, form a right handed frame.

For a given line, if it corresponds to an external bone pixel in the x-ray image, the method determines whether there are any apparent contours that it pierces. If so, retain the pierced apparent contour for which the distance to the closest point is the largest. Otherwise, retain the apparent contour for which the distance to the closest point is the smallest.

If the line corresponds to an internal bone pixel in the x-ray image, the method determines whether there are any apparent contours that it does not pierce. If so, retain the apparent contour that is not pierced for which the distance to the closest point is the largest. Otherwise retain the apparent contour that is pierced and for which the distance to the closest point is the smallest.

In the sixth stage, the method uses the line to points correspondences that were established in the fifth stage and computes the rotation and translation that registers them as explained elsewhere in this patent application.

The third through sixth stages are repeated until either of the following applies: 1) the sum of distances between the lines and points falls below a predetermined threshold value; 2) the angle of the rotation and the magnitude of the translation fall below a predetermined threshold value; or 3) a maximum allowable number of iterations is reached.

Additional distinctions between the foregoing approach and the method of Lavallee et al., with respect to differences already discussed previously, is that they define a distance function in a volume of space and implicitly assume that the surface model is a closed and oriented surface, or an oriented surface without boundaries. A closed and oriented surface separates the underlying space in two subspaces, the inside and the outside. An oriented surface with boundaries does not separate the space into an inside and an outside. However, in clinical applications, there is often not enough data to define the model of a closed surface, because slices are missing in the top or in the bottom of the surface, or because a portion of anatomy defined by the surface was not scanned.

Additional differences between the foregoing method and the Feldmar et al. method is that they define corresponding points between the x-ray images and a surface model. Because they do not use the surface apparent contours as employed herein, their method for finding corresponding points searches over a much larger set of potential correspondences, and is thus more expensive and may be prone to generate incorrect correspondences.

Mathematical Formulation

The approach of this invention is to minimize the sum of squared distances between a set of m 3-D vertices $\{p_i\}$ and corresponding m 3-D lines $\{(c_i, v_i)\}$, passing through a given center of perspective $c_i$ and having the direction of the unit vector $v_i$, $\|v_i\|=1$. In the following, Q represents a 3-D rotation matrix and t represents a 3-D translation vector. Q and t are the unknown, and all the other symbols have known values or expressions. The distance $d_i$ between the transformed 3-D point $Q_{pi}+t$ and the ith. 3-D line $(c_i, v_i)$ is obtained by taking the norm of the cross product between the vector joining $c_i$ and $Q_{pi}+t$ and the unit vector $v_i$ that specifies the direction of the line.

The problem can be written as follows:

Problem 1

$$\min_{Q,t} \sum_{i=1}^{m} d_i^2 = \min_{Q,t} \sum_{i=1}^{m} \|V_i(c_i - (Q_{pi} + t))\|^2, \quad (1)$$

where $V_i$ denotes the skew symmetric matrix $$V_i = \begin{bmatrix} 0 & -v_3 & v_2 \\ v_3 & 0 & -v_1 \\ -v_2 & v_1 & 0 \end{bmatrix},$$

implementing the vector cross product with $(v_1, v_2, v_3)^t$. Solutions exist for any number of data points and lines provided that there is at least one point. However, it is known that a minimum of three points are required to provide a unique solution.

One parametrization of the rotation that is convenient for the formulation is one by Cayley found in Hermann Weyl, "The Classical Groups", Princeton, 1939, which is explained next. U is a skew symmetric matrix obtained from the vector u, i.e., $$U_i = \begin{bmatrix} 0 & -u_3 & u_2 \\ u_3 & 0 & -u_1 \\ -u_2 & u_1 & 0 \end{bmatrix},$$

then 3×3 matrix $Q=(I-U)(I+U)^{-1}$ is a rotational matrix. This particular parametrization has the following advantages. First, it is straightforward to linearize the rotation, resulting in $Q\sim I-2U$. Second, when the rotation is small, the parameter values correspond to the magnitude of rotation along the Cartesian axes. The computation involves rational expressions of the rotation parameters that are simpler to compute than sines and cosines.

Non-Linear Minimization

Consider first the expression (1) given above as the sum of squares of m real-valued functions $f_i(x)$ of n=6 variables, $x=(u_1, u_2, u_3, t_x, t_y, t_z)^t$, with:

$$f_i(x)=d_i=\|V_i(c_i-(Q_{pi}+t))\|. \quad (2)$$

One can rewrite the problem 1-equation (1) as:

$$\min_x \sum_{i=1}^{m} \|fi(x)\|^2 = \min_x \|f(x)\|^2, \quad (3)$$

where f is the vector $(f_1, \ldots, f_m)^t$. To minimize (3), the Levenberg Marquardt method can be used, which consists of switching gradually from Newton's minimization method to the steepest descent method. Since details on these methods are known (see, for example, Gill et al., "Practical Optimization", Academic Press, 1993), it is sufficient to briefly recall the principles and to concentrate instead on providing suitable input to library routines that implement these methods.

Newton's method supposes that a quadratic approximation of $\|f(x+y)\|^2/2$ is available for a small $\|y\|$:

$$\frac{\|f(x+y)\|^2}{2} = \frac{\|f(x)\|^2}{2} + g^t y + y^t H y$$

where g denotes the gradient of $$\frac{\|f\|^2}{2}$$

and H the Hessian, or symmetric matrix of second-order partial derivatives. By application of the chain rule, one obtains $g=J^t f$, where J is the gradient of f, which is a m by 6 matrix. Further differentiation leads to $H \approx J^t J$, provided that the error residual $\|f\|$ is small with respect to $\|J\|$. Newton's method consists of computing the value of y that will minimize the quadratic term, which corresponds to solving $J^t J y + J^t f = 0$. For numerical reasons, it is preferable to minimize the following, which is less sensitive to roundoff errors:

$$\min_y \|Jy+f\|.$$

The Levenberg Marquardt method consists of solving:

$$(J^t J + \lambda I)y + J^t f = 0$$

For a small $\lambda$ it corresponds to Newton's method, and for a large $\lambda$, y is determined by the formula $$y = -\frac{J^t f}{\lambda},$$

which corresponds to the steepest descent method along the direction of the gradient. In practice, $\lambda$ is set to a very small value at the beginning and gradually increased as the solution vector is approached.

It is necessary to provide the Levenberg Marquardt implementation with procedures for computing both f and J for any input parameters x. The value of f is easily computed by first deriving the rotation Q from $(u_1, u_2, u_3)$ and by using the formula (2). The gradient requires more computation, and the derivatives with respect to the translation parameters are the simplest:

$$\frac{\partial f_i}{\partial t} = \frac{V_i^t V_i (Q p_i - c_t + t)}{f_i}$$

In order to compute the derivative of $f_i$ with respect to u, considerable simplification is obtained by computing the derivatives of the vector $Qp_i$ with respect to u, which is a 3 by 3 matrix:

$$\frac{\partial Q p_i}{\partial u}.$$

One can write:

$$\frac{\partial f_i}{\partial u} = \left(\frac{\partial Q p_i}{\partial u}\right)^t \frac{V_i^t V_i (Q p_i - c_i + t)}{f_i}.$$

The method requires that the 6 by 6 matrix $J^t J$ be of full rank. It is thus necessary to provide at least 6 corresponding points and lines. It will be seen that the Linear method described next does not have this requirement.

Linearization and Constrained Minimization

The second method has been referred to above as the Linear method, and involves linearizing the rotation. The minimization is subjected to the constraint that the rotation will be small for the linearized equation to be valid.

After linearizing the rotation Q with I–2U, and constraining $\|u\|$ to be smaller than r, real value, (such as 1, in order to guarantee that the approximation holds true up to at least 2 decimal places in each rotation entry) the expression (1) becomes:

Problem 2

$$\min_{U,t} \sum_i \|V_i(c_i - (I - 2U)p_i - t)\|^2 + \lambda(r^2 - \|u\|^2) \quad (4)$$

Next the expression (4) is transformed and the method introduces the skew symmetric matrices $P_i$ (the relationship between $P_i$ and $p_i$ is the same as the one between U and u):

$$\min_{u,t} \sum_i \|V_i(P_i - C_i + 2P_i u + t)\|^2 + \lambda(r^2 - \|u\|^2), \quad (5)$$

which can rewritten in matrix form:

$$\min\|Ax - b\| \text{ subject to } \|Bx\| < r \text{ with} \quad (6)$$

$$A = \begin{vmatrix} 2V_1 P_1 & V_1 \\ \ldots & \ldots \\ 2V_n P_n & V_n \end{vmatrix}, 3n \times 6 \text{ matrix } x^t = (u^t, t^t),$$

The preferred technique for solving the equation is known as Generalized Singular Value Decomposition, which is explained in Golub et al., "Matrix Computations", chapter 12, pages 562–564, The John Hopkins University Press, 1993.

This method is iterative: once u, t have been estimated, the method computes Q from u, sets the new 3-D points $p_i = Qp_i + t$, and solves equation (6) until the increments of u, t are below a certain small value, or until a maximum number of iterations has been exceeded. Contrary to the LM method, any number of points greater than two can be fed to equation (6). An answer would normally be obtained with one point only, but it has been preferred to only consider problems with more equations than unknowns. The method works very well for three points and thus offers a good alternative to closed form solutions (see, for example, Fishler et al., "Random sample consensus: a paradigm for model fitting with applications to image processing and automated cartography", Graphics and Image Processing, 24(6):381–395, June 1981, ACM).

Use of the Robust M-Estimator

The third, presently preferred method is referred to as the Robust method. Robust is meant to convey that the method is resistant to outliers. The description begins with the expression minimized in (5), with the difference being that each individual error term, or 3-D distance point-line that is weighted by-specifically, becomes the argument of a function ρ, such that measurements that correspond to an error exceeding the median of the errors by some factor have a constant contribution. This formulation was introduced by Tukey, and ρ is referred to as the Tukey weighting function.

Problem 3

$$\min_{u,t} \Delta = \sum_i \rho\left(\frac{\|V_i(p_i - c_i + 2P_i u + t)\|}{s}\right) \quad (7)$$

where s is a scale factor. If we denote $e_i = \|V_i(p_i - c_i + 2P_i u + t)\|$ the error, then the constant s can be defined as:

$$s = \frac{\text{median}(e_i)}{.6745}.$$

It is not necessary to know the exact expression of ρ. Instead, use the derivative of ρ, ψ, which has the following expression:

$$\psi(u) = \begin{bmatrix} u \\ 0 \text{ otherwise} \end{bmatrix} (1 - u^2/a^2)^2 \text{ if } \|u\| \le a.$$

Following the approach of Kumar et al., set a=2. Note that the choice of a, as well as the choice of s, influence the proportion of data points that will be considered as outliers. Contrary to before, one cannot solve equation (7) directly, and it must instead be differentiated with respect to u, t. The first step is to differentiate $e_i$ with respect to u and t.

$$\frac{\partial e_i}{\partial u} = \frac{\partial \sqrt{(p_i - c_i + 2P_i u + t)^t V_i^t V_i (p_i - c_i + 2P_i u + t)}}{\partial u}$$

$$= \frac{2P_i^t V_i^t V_i (p_i - c_i + 2P_i u + t)}{2e_i}$$

$$\frac{\partial e_i}{\partial t} = \frac{V_i^t V_i (p_i - c_i + 2P_i u + t)}{2e_i}$$

At this point the projection matrix is introduced:

$$W_i = V_i^t V_i = I - v_i v_i^t.$$

The derivative of Δ with respect to the vector u yields, once the constant terms have been removed from the summation:

$$\frac{\partial \Delta}{\partial u} = 0 = \sum_i \psi\left(\frac{e_i}{s}\right) \frac{P_i^t W_i(p_i - c_i + 2P_i u + t)}{e_i}$$

$$\frac{\partial \Delta}{\partial t} = 0 = \sum_i \psi\left(\frac{e_i}{s}\right) \frac{W_i(p_i - c_i + 2P_i u + t)}{e_i}$$

which can be rewritten in matrix form:

$$Cx = d \text{ with } C = \sum_i \psi\left(\frac{e_i}{s}\right) \begin{vmatrix} -2P_i^t W_i P_i & -P_i^t W_i \\ 2W_i P_i & W_i \end{vmatrix}, 6 \times 6 \text{ matrix}, \quad (8)$$

$$x^t{}_i = (u^t, t^t),$$

$$d = \sum_i \psi\left(\frac{e_i}{s}\right) \begin{vmatrix} -P_i^t W_i(c_i - p_i) \\ W_i(c_i - p_i) \end{vmatrix}, 6 \times 1 \text{ vector.}$$

The method can be applied to any number ($\geq 1$) of points. However, in the case of three points, an exact match for all points is possible and it has been observed that the Linear method is more accurate, since the normal least squares equations (8) are used rather than the direct minimization.

In practice, the Linear Method equation (6) has been implemented with an explicit constraint $\|u\|$ being smaller than r, while the Robust method, equation (8), has been implemented without constraint.

Comparison of the Methods

To compare the LM, Linear and Robust methods, it is convenient to generate a set of lines and points that simulate a typical configuration that would occur when solving a pose estimation problem specialized to radiographic imagery.

Figure 4:
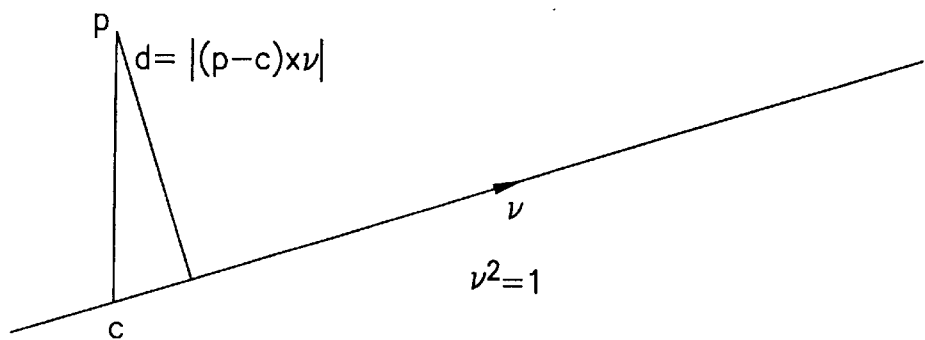
FIG. 4 illustrates an equation that is solved in the method for registering a point to a three dimensional infinite line, and shows, more specifically, the Euclidian distance d between a 3-D line defined with a vertex c, a unit direction v, and a 3-D point p.
Figure 11A:
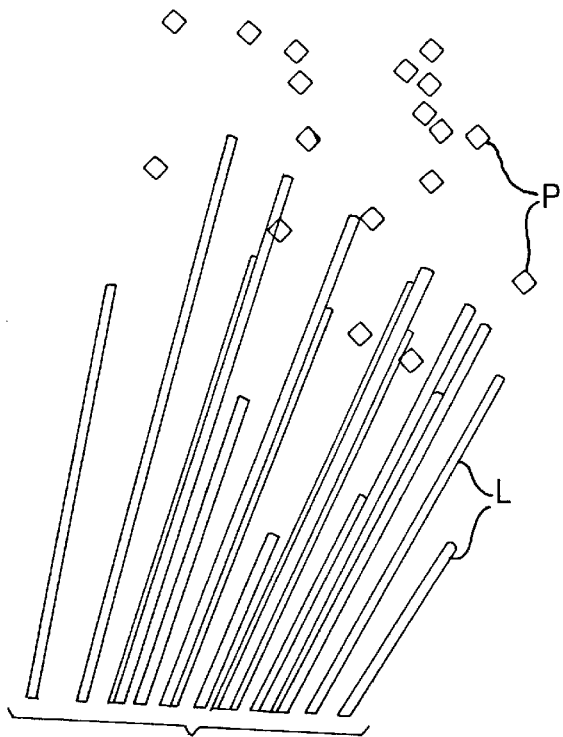
FIGS. 11A and 11B illustrate a configuration of points (P), represented as tetrahedra of different intensities, and lines (L), shown as thin parallelepipeds, before (FIG. 11A) and after (FIG. 11B) registration. Although one of the points, surrounded with a rectangle (R), was perturbed with noise, the remaining points were successfully registered.
Figure 11B:
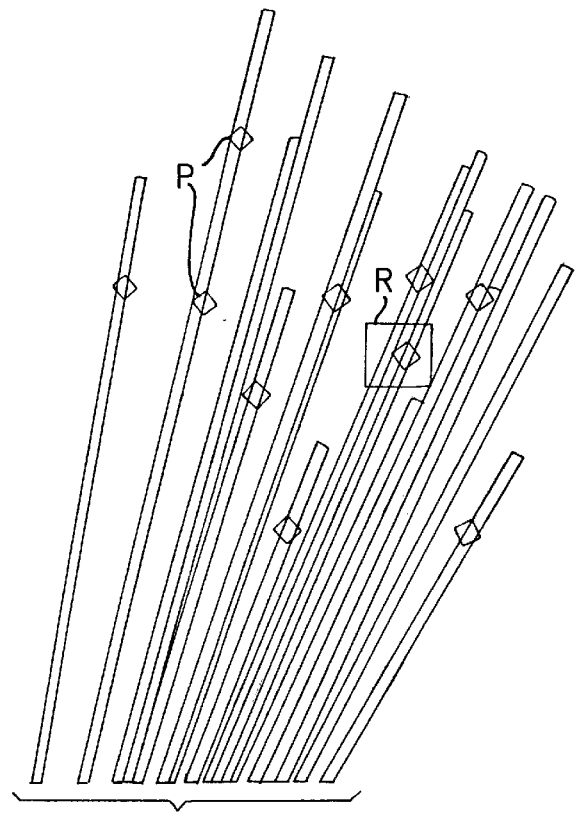

The first step is to generate the base configuration of points and lines. First choose m random points $\{p\}_{i=1}, \ldots,$ m inside a unit cube: $0 \leq x,y,z \leq 1$, and assume a perspective projection. The following step is performed to choose a center of perspective c, where all lines will intersect. Reference can also be had to FIG. 4. Place c along the line of equation x=y=z, and then cast a ray between c and each $p_i$, obtaining a direction $v_i$. For this example, the point (-2, -2, -2) was chosen which corresponds to a maximum angle for the bundle of lines of approximately 20 degrees. In order for the result to be independent of the particular choice for the origin and axes, rotate the entire configuration by a rotation of random axis and of arbitrary angle (e.g., 30 degrees). Then rotate the points $\{p_i\}$ only by a random rotation of 30 degrees, which is within the range of expected rotations for the pose estimation problem. Next translate the points by a random vector that has the same magnitude as the points—the random vector is drawn inside the unit cube. This completes the construction of the base configuration. A base configuration of 20 points and lines is shown in FIGS. 11A and 11B.

The next step is to take the base configuration, register the points to the lines, and then compare the transformation obtained with the one that was effectively applied. In order to make the comparison, apply both transformations to landmark or reference points and compute the distance between the two transformed points. Next choose the vertices of the unit cube as landmark points (1,0,0), (0,1,0) and (0,0,1). The maximum distance, or maximum error, is chosen to measure the quality of registration.

The last step is to add noise to selected points, thereby simulating the noise present in typical radiographic images. This is accomplished by adding zero mean Gaussian noise to the points. The maximum standard deviation of the noise varies from 0 to 0.33, which is roughly one third of the diameter of the cloud of points. This amount of noise is rarely observed in practice. In this example noise can be added to a selected number of points, up to 50%.

Figure 12A:
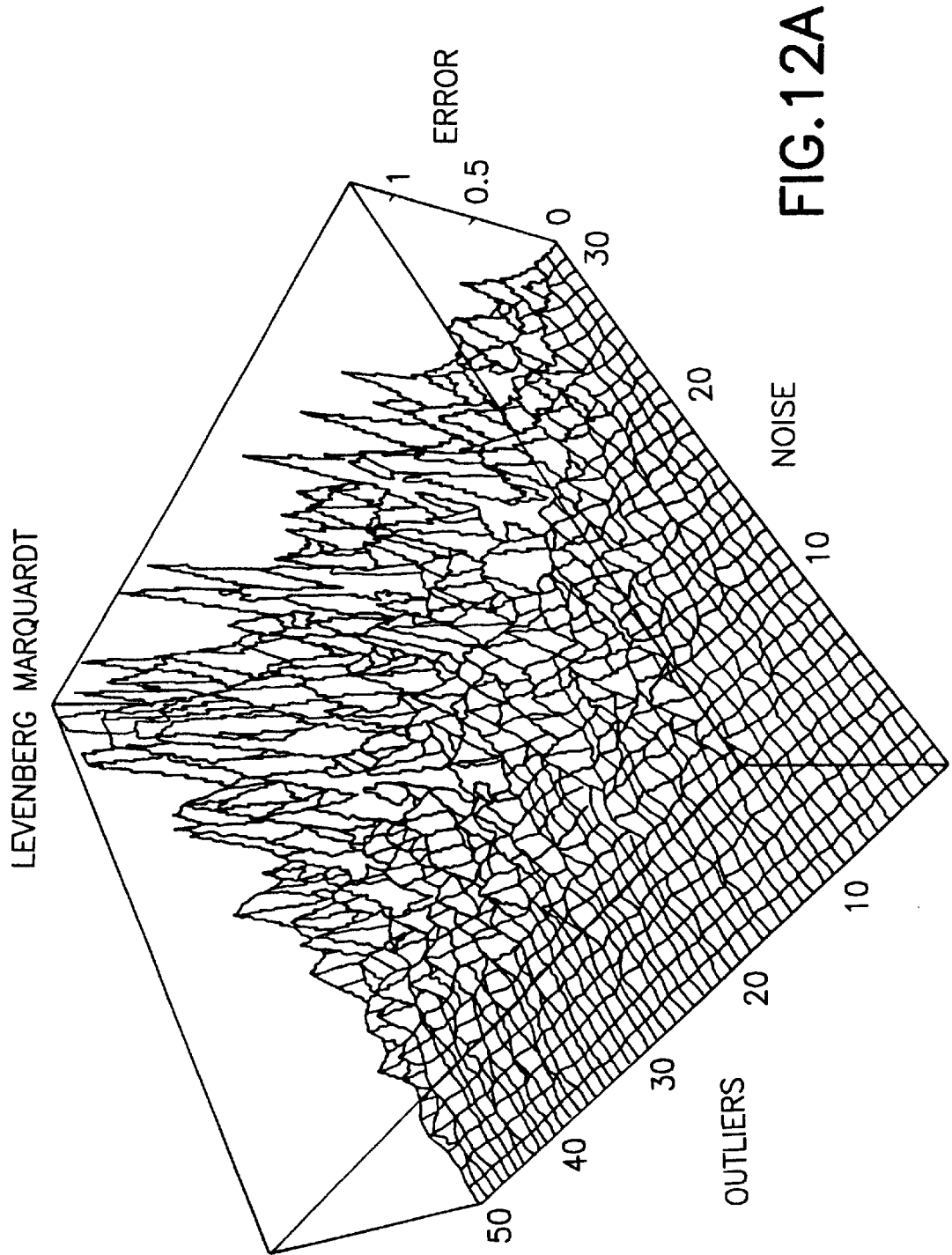
FIG. 12A is a graph that illustrates a maximum registration error plotted vs. noise magnitude and percentage of outliers for a LM (Levenberg Marquardt) method for registering 3-D points to 3-D lines, which is useful for estimating the pose of 3-D anatomical surface models and images in one or several 2-D images.
Figure 12B:
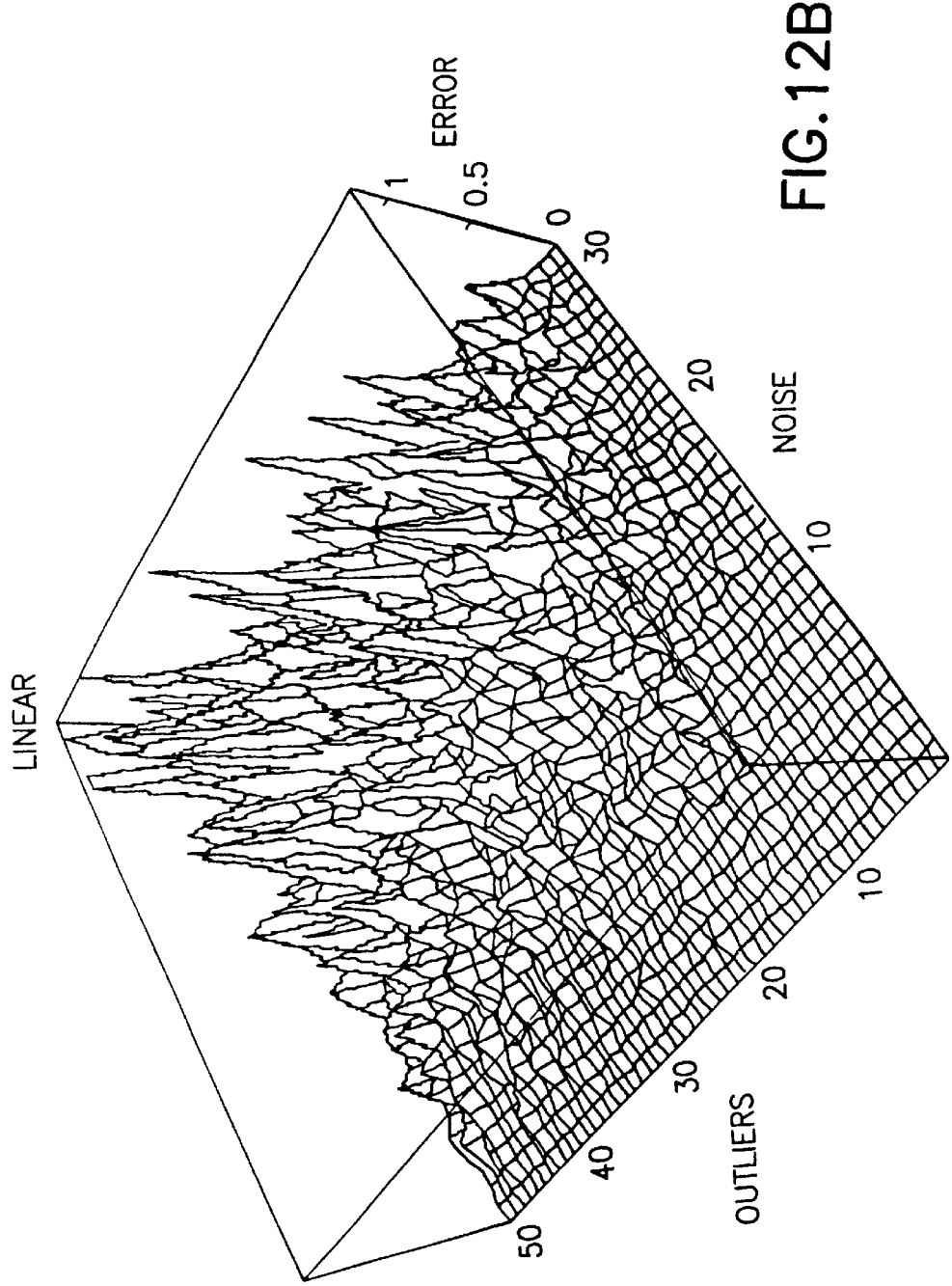
FIG. 12B is a similar graph that illustrates a maximum registration error for a Linear method.
Figure 13A:
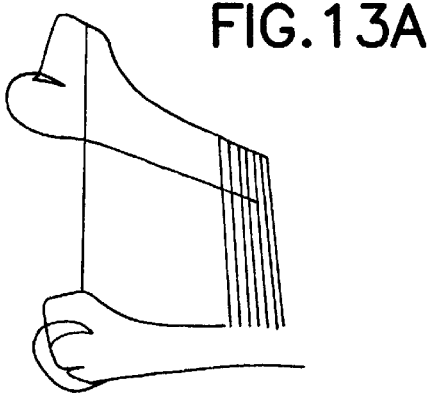
FIGS. 13A–13F are a temporal series or sequence of "snapshots" of an operation of a surface to profile registration method, observed from the camera used to generate the first profile.
Figure 13B:
Figure 13C:
Figure 13D:
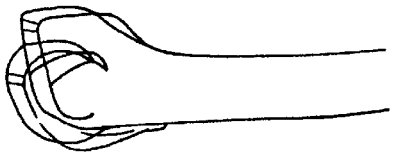
Figure 13E:
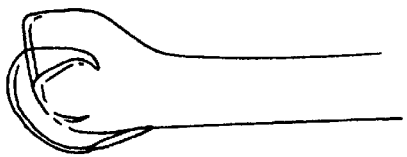
Figure 13F:
Figure 14A:
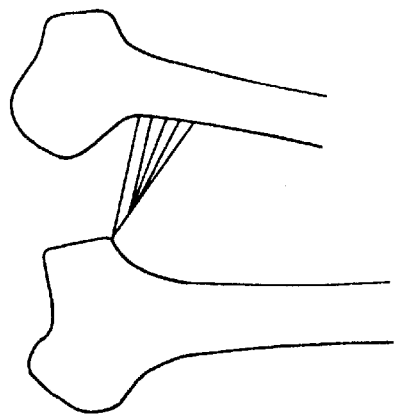
FIG. 14A–14F are a similar temporal series of snapshots of the registration method taken from a second viewpoint.
Figure 14B:
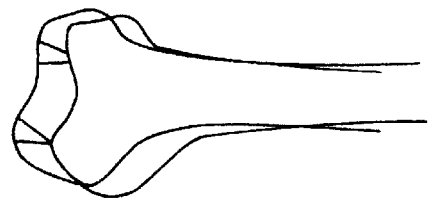
Figure 14C:
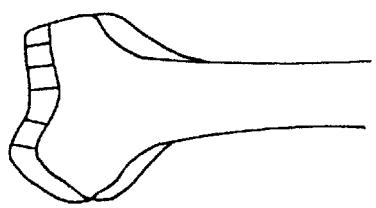
Figure 14D:
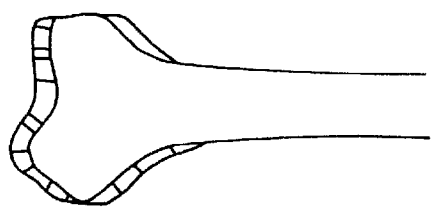
Figure 14E:
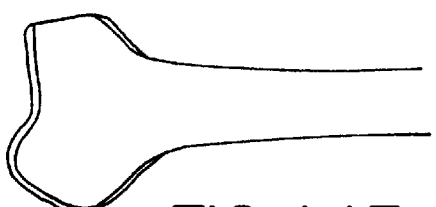
Figure 14F:
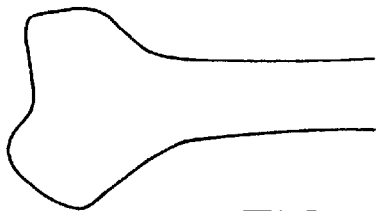

FIGS. 12A, 12B and 12C show the maximum registration error with each method. These figures show that the LM and Linear methods typically tolerate noise that does not exceed about 10% of the diameter of the cloud of data points. Noise of higher magnitude can be accommodated provided that less than 5% of the points are corrupted by noise.

While in theory the Robust method should operate with up to 50% of spurious points, in practice, such a large number of outliers has been found to be tolerated only with small noise levels. Successful registration has been observed with up to approximately 40% of outliers corrupted with noise of magnitude a third of the diameter of the cloud of data points.

Registration of a Surface Model to its Projections

The registration of a 3-D object to a 2-D projection, or pose recovery, involves finding the 3-D position and orientation, or pose, of the camera that would have produced the given projection. Alternatively, the problem can be seen as, given a predefined pose for the camera, finding the pose of the object that would have produced the projection. The availability of several projections can help to constrain the pose further, and to obtain a more accurate estimate. It is assumed herein that the internal calibration parameters of the camera are known. For example, for a perspective projection, the focal length, image center and scale parameters of the camera are known. If there is distortion, it is assumed to have been compensated for.

In medical imaging, a related goal is to register 3-D volumetric data, such as that obtained for a CT-scan, to a 2-D radiographic image. Such a registration is used, in accordance with a preferred embodiment of this invention, to correlate a surgical plan, that is based upon the 3-D CT-scan data, with the accurate location of a patient on the operating table.

The Robust method was used for testing the registration of a surface model to two projections. A surface model of a human femur was built starting from a CT scan of a dry bone. The image of the bone was separated from the image of a fiducial system that had been attached to it. An iso-surface was then extracted which contained 100K vertices. The surface was then approximated with a triangulated surface containing 1500 vertices.

In order to simulate radiographs taken through the femur model, two perspective profiles of the femur model were generated with different camera orientations, differing by 40 degrees, which are referred to as target profiles. The size of the model, which was extracted from a CT-scan, reflected the size of a typical human femur. To model the camera, a focal length of 1000 mm was selected, which is typical of a plain film radiograph. The profiles were obtained by first constructing the apparent contour of the surface as a collection of closed 3-D non-planar curves, and then projecting the apparent contours onto the focal planes of the cameras, wherein the apparent contour is the locus of all points of the surface such that the tangent plane and viewing direction are parallel. On a triangulated surface with certain regularity properties, the apparent contour can be defined as a set of closed and oriented curves.

To pose was then perturbed with a series of random rotations and translations. For each perturbation, the method was able to relax to pose of the surface to its original location. The algorithm used in this embodiment of the invention was as follows. (A) Using the current pose, generate two profiles, one for each view, which are referred to as transient profiles. (B) The transient profiles were then superimposed onto the target profiles. (C) For each point of the target profiles, compute the closest point on the transient profile, thus hypothesizing correspondences. (D) The correspondences found were then filtered to retain those that globally contributed to the same 2-D transformation.

This second method thus infers corresponding points and lines in 2-D, whereas in the preferred embodiment described previously the line to point correspondences are inferred in 3-D by directly finding the closest point from the line to the apparent contour. In the second method, illustrated in FIGS. 13A–13F and 14A–14F, the closest points are computed in 2-D, and from the 2-D correspondence both a 3-D line and a 3-D point are inferred.

As the target profiles were perfectly calibrated, a ray can be cast in space from the center of perspective to the profile, and as the transient profiles have been projected from the surface, one could save the position on the apparent contour of the corresponding surface point. Hence, for each transient profile, the problem was reduced to registering 3-D surface points to 3-D lines. The points and lines were then inputted to the Robust method, and the transformation found was applied to the surface.

The final solution, shown in FIGS. 13A–13F and 14A–14F, was obtained by iterating on the above process until the transformation found by the Robust method corresponded to the identity transformation.

A total of sixty different rotations were applied with a random axis and angles ranging from ten to sixty degrees. The registration accuracy was measured by selecting three points on the surface, two on the condyles and one on the trochanter, in order to simulate the metallic pins used for clinical procedures. The original position of these "markers" was then compared to the final one obtained by applying the perturbation plus the transformation found by the Robust method. The largest distance between corresponding markers, reflecting the maximum registration error, was reported on a graph. As for most initial rotations, the maximum error was well below one mm, some misregistrations could be observed for perturbations exceeding 30 degrees of rotation, which are unlikely to be observed in practice.

One of the advantages of generating profiles and using correspondences between 3-D lines and apparent contours of the surface is that the registration can be performed quickly, e.g., within 13 seconds on an IBM RS6000 Workstation, representing the processing of both views and the creation of snapshots. Again, the overall registration process corresponds to solving many instances of the lines to points registration problem. Another advantage is that one can readily visually determine on the 2-D projection whether the registration is accurate, whereas a 3-D view can be useful for providing three dimensional spacial relationships. Note that the registration error is measured in 3-D using the final pose, lines and points.

While the invention has been particularly shown and described with respect to preferred embodiments thereof, it will be understood by those skilled in the art that changes in form and details may be made therein without departing from the scope and spirit of the invention.

What is claimed is:

1. A method for registering two dimensional fluoroscopic images with a three dimensional model of a surgical tissue of interest, comprising steps of:

(a) generating a three dimensional model of a surgical tissue of interest using a plurality of images of the surgical tissue of interest;

(b) obtaining at least two, two dimensional fluoroscopic images representing at least two views of the surgical tissue of interest, the images containing markers for associating an image coordinate system with a surgical coordinate system;

(c) detecting the presence of first contours of the surgical tissue of interest in each of the at least two views;

(d) deriving bundles of lines in three dimensional space that pass through the detected first contours; and (e) iteratively matching points in three dimensional space on second contours obtained from the three dimensional model with the bundles of lines in three dimensional space until the three dimensional model is registered within the surgical coordinate system to a predetermined level of accuracy.

2. A method as in claim 1, wherein the step of generating a three dimensional model includes preliminary steps of performing a plurality of scans through the surgical tissue of interest to generate a plurality of image slices, and processing the image slices to generate a three dimensional model of the surface of the surgical tissue of interest.

3. A method as in claim 1, wherein the step of obtaining at least two, two dimensional fluoroscopic images includes steps of positioning a calibration device within a field of view of a fluoroscopic imaging system, the calibration device containing radio-opaque markers having a predetermined shape, and processing the two dimensional images to locate edges of images of the markers.

4. A method as in claim 3, wherein the step of positioning includes a step of translating the calibration device through the field of view using a robot manipulator, the calibration device being translated along a first ruled surface and along a second ruled surface that is generally parallel to the first ruled surface, the first and second ruled surfaces each being generally perpendicular to an optical axis of the fluoroscopic imaging system.

5. A method as in claim 4, wherein the calibration device has a generally circular cylindrical rod-like shape having the radio-opaque markers spaced apart along a longitudinal axis of the calibration device.

6. A method as in claim 3, wherein the step of positioning includes a step of mounting the calibration device within a field of view of a camera that forms a portion of the fluoroscopic imaging system.

7. A method as in claim 4, wherein the calibration device has a first set of radio-opaque markers located in a first plane, and a second set of larger radio-opaque markers located in a second plane, and wherein the first plane is located further from a source of imaging radiation than the second plane and is generally parallel to the second plane, the first and second planes each being generally perpendicular to an optical axis of the fluoroscopic imaging system.

8. A method as in claim 1, wherein the step of iteratively matching includes steps of:

defining a distance between points on the surfaces of the model and a beam of lines in three dimensional space that approach the surfaces; and finding a pose of the surfaces that minimizes a distance to the lines from the points.

9. A method as in claim 1, wherein the step of iteratively matching includes a step of minimizing a sum of positive measures of a Euclidean distance between each point and its corresponding line.

10. A method as in claim 9, wherein the step of minimizing employs one of a non-linear Levenberg Marquardt minimizer, or a Linear minimizer followed by constrained minimization, using a sum of squared distances between points and lines.

11. A method as in claim 9, wherein the step of minimizing employs a statistically Robust minimizer that weights each squared distance between a point and a line in the sum with a function that favors distances that are similar to a median of the distances.

12. A method as in claim 1, wherein the first contours are two dimensional contours and the second contours are apparent contours.

13. A method as in claim 1, wherein the surgical coordinate system is comprised of a robot coordinate system.

14. A robotically-assisted surgical system, comprising:
   a robot having an effector that is controllably positioned within a robot coordinate system;
   a first imaging device for obtaining two dimensional radiographic images a tissue of interest, the images containing markers obtained from a calibration device that is located within a field of view of the first imaging device and that is separate from the tissue of interest the markers being used for associating an image coordinate system with the robot coordinate system;
   a second imaging device for obtaining images of slices through the tissue of interest;
   a data processor having an input coupled to an output of the first and second imaging devices and an output coupled to the robot, said data processor generating a three dimensional model of the tissue of interest from the output of the second imaging device, said data processor further detecting a presence of two dimensional contours of the tissue of interest in each of at least two views of the tissue and deriving bundles of lines in three dimensional space that pass through the detected two dimensional contours; said data processor operating to iteratively match points in three dimensional space, that are located on three dimensional apparent contours that are associated with a surface of the three dimensional model, with the bundles of lines in three dimensional space until the three dimensional model is registered with the robot coordinate system to a predetermined level of accuracy, wherein said surface apparent contours are boundaries between visible and invisible surface triangles.

15. A robotically-assisted surgical system as in claim 14, wherein said calibration device is adapted for being robotically translated, external to a patient who comprises the tissue of interest, and within a field of view of said first imaging device, said calibration device having a rod-like shape and being comprised of a radiolucent material containing a plurality of radio-opaque markers that are spaced apart along a longitudinal axis of said calibration device.

16. A robotically-assisted surgical system as in claim 15, wherein said calibration device is robotically translated along a first plane and along a second plane that is generally parallel to the first plane, the first and second planes each being generally perpendicular to an optical axis of the first imaging device, wherein said radio-opaque markers are each sized so as to be capable of producing an image when said calibration device is translated within the field of view of the first imaging device.

17. A robotically-assisted surgical system as in claim 14, wherein said calibration device is adapted for being positioned within a field of view of said first imaging device and external to a patient who comprises the tissue of interest, said calibration device being comprised of a radiolucent body portion containing a first set of radio-opaque markers located in a first plane and a second set of larger radio-opaque markers located in a second plane, and wherein the first plane is located further from a source of imaging radiation of the first imaging device than the second plane and is generally parallel to the second plane, the first and second planes each being generally perpendicular to an optical axis of the first imaging device, said calibration device further comprising a plurality a robot reference locations on a surface thereof.

18. A system for registering two dimensional fluoroscopic images with a three dimensional model of a tissue of interest, comprising:
   a model processor for generating a three dimensional model of a tissue of interest using as input a plurality of images taken through the tissue of interest;
   an imaging system for obtaining, in cooperation with a calibration device, at least two, two dimensional images representing at least two views of the tissue of interest, the images containing calibration markers for associating an image coordinate system with a second coordinate system; and
   an image processor having inputs coupled to outputs of said model processor and said imaging system for detecting the presence of first contours of the tissue of interest in each of the at least two views, said image processor operating to derive bundles of lines in three dimensional space that pass through the detected first contours, and further operating to match points on second contours obtained from the three dimensional model with the bundles of lines in three dimensional space until the three dimensional model is registered within the second coordinate system to a predetermined degree of accuracy.

19. A system as in claim 18, wherein said model processor uses a plurality of image slices obtained from a plurality of scans through the tissue of interest, and processes the image slices to generate a three dimensional model of the surface of the tissue of interest.

20. A system as in claim 18, wherein said system further comprises a robot manipulator for translating said calibration device within a field of view of said imaging system, said calibration device comprising said calibration markers, and wherein said image processor processes the two dimensional images to locate images of said calibration markers within said two dimensional images.

21. A system as in claim 18, wherein said system further comprises a robot manipulator for translating said calibration device within a field of view of said imaging system, said calibration device comprising said calibration markers, wherein said robot manipulator is controlled for translating said calibration device within a first ruled surface and within a second ruled surface that is spaced apart from the first ruled surface.

22. A system as in claim 20, wherein a composite image of said calibration markers is comprised of a plurality of images of said calibration device located at a plurality of different locations within the field of view of said imaging system.

23. A system as in claim 18, wherein said calibration device has a generally circular cylindrical rod-like shape, and wherein said calibration markers are comprised of radio-opaque material and are spaced apart from one another along a longitudinal axis of said calibration device.

24. A system as in claim 18, wherein said calibration markers are comprised of radio-opaque material, wherein said calibration device comprises a first set of said calibration markers that are disposed in a first plane and a second set of larger calibration markers that are located in a second plane, wherein said first plane is located closer to a source of imaging radiation of said imaging system than said second plane and is generally parallel to said second plane, and wherein said first plane and said second plane are each generally perpendicular to an optical axis of said imaging system.

25. A system as in claim 18, wherein the second coordinate system is comprised of a robot coordinate system.

26. A system as in claim 18, wherein the tissue of interest is comprised of bone, and wherein said imaging system comprises means for obtaining images of bone through overlying tissue.

27. A method for generating a three dimensional model of a tissue of interest and for aligning the three dimensional model with two dimensional images of the tissue of interest, comprising steps of:

performing a plurality of imaging scans through the tissue of interest to generate a plurality of two dimensional image slices;

processing the image slices to generate a three dimensional model of a surface of the tissue of interest;

obtaining a plurality of two dimensional images representing at least two views of the tissue of interest, the at least two views also comprising images of calibration markers for associating an image coordinate system with a second coordinate system;

detecting first contours of the tissue of interest in each of the at least two views;

deriving bundles of lines in three dimensional space that pass through the detected first contours; and matching points on second contours obtained from the surface of the three dimensional model with the bundles of lines until the three dimensional model is aligned within the second coordinate system to a predetermined level of accuracy.

28. A method as in claim 27, wherein the step of processing the image slices to generate a three dimensional model is comprised of the steps of:

extracting outer contours of the tissue of interest for each image slice to obtain at least one and typically a plurality of polygonal curves representing contours of the tissue of interest.

replacing the polygonal curves with approximating polygonal curves containing fewer vertices, such that the approximating polygonal curves do not deviate from the original polygonal curves by more than a pre-specified threshold, wherein each polygonal curve is represented using an ordered array of vertices, and each vertex is indexed with its position in the array;

building a surface model comprised of triangles that contains every vertex and every edge of the approximating polygonal curves, the step of building a surface model examining in turn pairs of consecutive image slices and constructing a surface slab that contains the approximating polygonal curves extracted from both image slices; and combining the surface slabs to form a resulting surface by removing duplicate references to vertices belonging to polygonal curves shared by any two slabs.

29. A method as in claim 28, and further comprising a step of:

approximating the resulting surface with a surface containing fewer triangles by the use of a surface simplification technique.

30. A method as in claim 28, wherein the step of extracting comprises steps of:

selecting a plurality of points within an image slice in the vicinity of a structure of interest;

constructing a polygonal curve linking the selected points; and modifying the polygonal curve to minimize an expression that combines a measure of curve length, a measure of average curvature of the curve, a measure of an image potential average curvature of the curve, and a measure of an image potential.

31. A method as in claim 30, wherein the image potential equals the squared norm of the image gradient, where if I(x,y) is the image intensity of a pixel of location (x,y), the image gradient grad (I) is a vector whose first coordinate is the derivative of I with respect to x, and whose second coordinate is the derivative of I with respect to y.

32. A method as in claim 28, wherein the step of replacing comprises steps of:

for each polygonal curve, iterating the following steps (a)–(c) until a maximum deviation threshold is respected,
(a) computing the maximum deviation between any vertex and a line segment obtained by joining the last vertex with the first vertex;
(b) if the maximum deviation computed is larger than the threshold, splitting the ordered array of vertices into two arrays; and
(c) considering two polygonal curves defined with the resulting split arrays.

33. A method as in claim 28, wherein the second contours are surface apparent contours defined as boundaries between visible and invisible surface triangles, wherein a visible triangle is one that a ray cast from a focal point of the lines to the triangle centroid makes an obtuse angle with the triangle normal direction, wherein surface apparent contours can be constructed as a set of closed, oriented, non-planar polygonal curves.

34. A method as in claim 27, wherein multiple images of calibration markers are superimposed to form a calibration marker grid, the images being obtained for a plurality of different locations of a calibration device within a field of view of a tissue imaging system.

35. A method as in claim 27, wherein images of calibration markers are processed using Thin Plate Spline functions to determine lines in three dimensional space representing a path of imaging radiation.

* * * * *